(12) United States Patent
Takiguchi et al.

(10) Patent No.: US 9,772,361 B2
(45) Date of Patent: Sep. 26, 2017

(54) MEASURING METHOD AND MEASURING APPARATUS TO DETECT CHARGE POTENTIAL BETWEEN TIRE AND ROAD SURFACE

(71) Applicants: THE UNIVERSITY OF TOKYO, Bunkyo-ku, Tokyo (JP); BRIDGESTONE CORPORATION, Chuo-ku, Tokyo (JP)

(72) Inventors: Kiyoaki Takiguchi, Bunkyo-ku (JP); Yoshihiro Suda, Bunkyo-ku (JP); Shigeyuki Yamabe, Bunkyo-ku (JP); Kenji Kouno, Bunkyo-ku (JP); Tatsuo Hayashi, Kodaira (JP); Kotaro Yamada, Kodaira (JP); Nobuo Masaki, Kodaira (JP)

(73) Assignees: THE UNIVERSITY OF TOKYO, Bunkyo-ku, Tokyo (JP); BRIDGESTONE CORPORATION, Chuo-ku, Tokyo (JP)

( * ) Notice: Subject to any disclaimer, the term of this patent is extended or adjusted under 35 U.S.C. 154(b) by 626 days.

(21) Appl. No.: 14/368,357

(22) PCT Filed: Dec. 26, 2012

(86) PCT No.: PCT/JP2012/083724
§ 371 (c)(1),
(2) Date: Jun. 24, 2014

(87) PCT Pub. No.: WO2013/099984
PCT Pub. Date: Jul. 4, 2013

(65) Prior Publication Data
US 2014/0350879 A1 Nov. 27, 2014

(30) Foreign Application Priority Data

Dec. 26, 2011 (JP) ................................ 2011-282858
Mar. 30, 2012 (JP) ................................ 2012-082405
(Continued)

(51) Int. Cl.
*G01R 29/12* (2006.01)
*B60T 8/172* (2006.01)
(Continued)

(52) U.S. Cl.
CPC .............. *G01R 29/12* (2013.01); *B60T 8/172* (2013.01); *G01L 17/00* (2013.01); *G01M 17/02* (2013.01);
(Continued)

(58) Field of Classification Search
USPC ........................................................... 702/70
See application file for complete search history.

(56) References Cited

U.S. PATENT DOCUMENTS 3,676,769 A 7/1972 Loepfe
5,641,900 A * 6/1997 Di Bernardo ......... G01L 17/005
73/146
(Continued)

FOREIGN PATENT DOCUMENTS

DE 19953488 C1 5/2001
JP 11-99812 A 4/1999
(Continued)

OTHER PUBLICATIONS

Communication dated Jul. 7, 2015 from the Japanese Patent Office issued in corresponding application No. 2012082405.
(Continued)

*Primary Examiner* — Paul D Lee
(74) *Attorney, Agent, or Firm* — Sughrue Mion, PLLC

(57) ABSTRACT

A charge potential distributed over a vehicle body resulting from the contact, separation, and friction between a tire and
(Continued)

a road surface is detected by a detecting unit provided with a sensing electrode that is disposed on the external surface of the vehicle body, a reference electrode that is disposed apart from the external surface of the vehicle body with a space therebetween, and a sensor amplifier that senses a potential between the sensing electrode and the reference electrode as a signal and amplifies the signal. And the amplitude of the charge potential detected by the detecting unit is monitored by a data processing unit, thereby making it possible to accurately identify not only the state of the road surface but also an internal pressure state of the tire, a wear state of the tire, and the like during vehicular travel.

13 Claims, 18 Drawing Sheets

(30) Foreign Application Priority Data

| Mar. 30, 2012 | (JP) | ................................. 2012-082416 |
| Mar. 30, 2012 | (JP) | ................................. 2012-082425 |
| Mar. 30, 2012 | (JP) | ................................. 2012-082451 |

(51) Int. Cl.
| G01L 17/00 | (2006.01) |
| G01M 17/02 | (2006.01) |
| G01N 19/02 | (2006.01) |
| G01R 29/24 | (2006.01) |
| G01N 27/60 | (2006.01) |
| G01N 27/22 | (2006.01) |

(52) U.S. Cl.
CPC ............ *G01N 19/02* (2013.01); *G01N 27/221* (2013.01); *G01N 27/60* (2013.01); *G01R 29/24* (2013.01); *B60T 2210/12* (2013.01)

(56) References Cited

U.S. PATENT DOCUMENTS

| 6,050,136 | A | * | 4/2000 | Hawkinson | ............. B60C 25/00 324/558 |
| 7,523,656 | B1 | * | 4/2009 | Blixhavn | ............. B60C 23/0411 73/146.5 |
| 2001/0020386 | A1 | * | 9/2001 | Mancosu | ............. B60C 99/003 73/146 |
| 2003/0156021 | A1 | * | 8/2003 | Tabata | ................. B60C 23/0416 340/442 |
| 2003/0192375 | A1 | * | 10/2003 | Sugai | .................... B60C 23/061 73/146 |
| 2007/0029027 | A1 | * | 2/2007 | Stoila | ..................... B29D 30/06 156/110.1 |
| 2007/0213912 | A1 | * | 9/2007 | Deur | ....................... B60T 8/175 701/82 |
| 2009/0056433 | A1 | | 3/2009 | Kvisteroey et al. | |
| 2010/0164705 | A1 | * | 7/2010 | Blanchard | ............. B60C 23/041 340/442 |
| 2011/0043375 | A1 | * | 2/2011 | Tanaka | ................. B60C 23/0408 340/870.07 |
| 2013/0174657 | A1 | * | 7/2013 | Beccavin | .............. G01M 17/02 73/146 |

FOREIGN PATENT DOCUMENTS

| JP | 11-108652 A | 4/1999 |
| JP | 2001-103652 A | 4/2001 |
| JP | 2008-37130 A | 2/2008 |
| JP | 2011-203017 A | 10/2011 |
| WO | 2004002758 A1 | 1/2004 |

OTHER PUBLICATIONS

International Search Report of PCT/JP2012/083724, dated Feb. 12, 2013.
Communication dated Aug. 6, 2015 from the European Patent Office issued in the corresponding European application No. 12862338.6.

* cited by examiner

NUMBER OF SPECIFIC PEAK OCCURRENCES [times]

ON DRY ROAD SURFACE

ON WET ROAD SURFACE

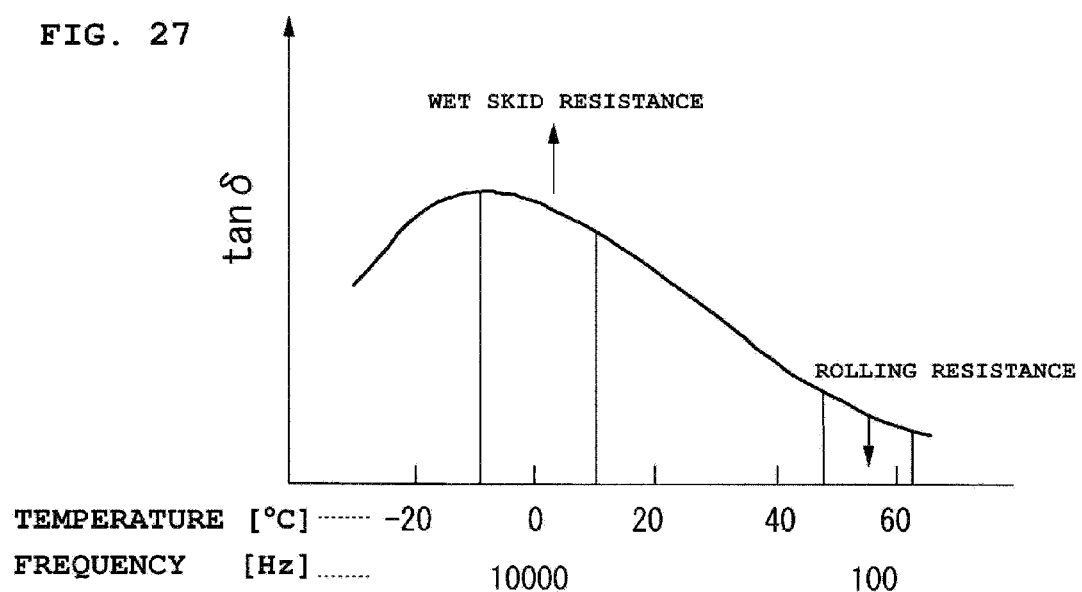

MEASURING METHOD AND MEASURING APPARATUS TO DETECT CHARGE POTENTIAL BETWEEN TIRE AND ROAD SURFACE

CROSS REFERENCE TO RELATED APPLICATIONS

This application is a National Stage of International Application No. PCT/JP2012/083724 filed Dec. 26, 2012, claiming priority based on Japanese Patent Application Nos. 2011-282858, filed Dec. 26, 2011, 2012-082405, filed Mar. 30, 2012, 2012-082416, filed Mar. 30, 2012, 2012-082425, filed Mar. 30, 2012 and 2012-082451, filed Mar. 30, 2012, the contents of all of which are incorporated herein by reference in their entirety.

BACKGROUND OF THE INVENTION

1. Field of the Invention

The present invention relates to a measuring method and apparatus for measuring quasi-electrostatic field occurring from contact between tires of a running vehicle and the road surface and, in particular, to a measuring method and apparatus which can be preferably applied to estimating the state of the road surface or detecting the running state of the tires.

2. Description of the Related Art

There have been technologies proposed for detecting the acceleration of a tire as an indicator in identifying the state of the road surface as disclosed in the prior art document listed below (see Patent Document 1).

PRIOR ART DOCUMENT

Patent Document

Patent Document 1: Japanese Unexamined Patent Application Publication No. 2011-203017

SUMMARY OF THE INVENTION

Problem to be Solved by the Invention

However, the laws of physics do not allow the use of acceleration in finding the material of the road surface or the differences of objects that exist between the tire and the road surface. In other words, acceleration can only be an indicator in indirectly identifying the state of the road surface.

Therefore, the above-mentioned technology cannot distinguish between a road surface wet with water, which is one of important states of the road surface to be identified, and a road surface laid with iron sheets, for example. Thus, the technology's accuracy in identifying the state of the road surface is not necessarily high.

The present invention has been made in view of the foregoing circumstances, and an object of the invention is to propose a measuring method and apparatus that offer enhanced identification of not only the state of the road surface but also the state of the tire.

Means for Solving the Problem

It is generally known that the contact, separation, and friction between tires and a road surface produce charge potentials of static electricity between the tires and the road surface. On the other hand, since a vehicle body and the tires are capacitively coupled to each other, potentials corresponding to the charge potentials having occurred between the tires and the road surface are generated on the external surface of the vehicle body.

The electric field distributed over the surface of tires or the external surface of a vehicle body is one of the electric fields generated at the distance r by a micro dipole antenna as expressed by equation (1) below. It can be derived as a solution to Maxwell's equations. Equation (1) includes three elements constituting an electromagnetic field (radiation field which is in proportion to $1/r$, induction field which is in proportion to $1/r^2$, and quasi-electrostatic field which is in proportion to $1/r^3$). The third term represents an electric field distributed over the tire surface or the external surface of a vehicle body, which changes with time as the tires rotate during vehicular travel.

$$E = j\frac{60\pi I}{\lambda}Ie^{-j\beta r}\left\{\frac{1}{r} + \frac{1}{j\beta r^2} + \frac{1}{(j\beta)^2 r^3}\right\}\sin\theta \quad \text{[Equation 1]}$$

The quasi-electrostatic field contains no magnetic-field component and has no propagation property as with radio waves. The quasi-electrostatic field is distributed, like electrostatically-charged fields, around persons, vehicles, and other materials, and its polarity or its level changes.

Through systematic investigations, the inventors have reached this invention by discovering that the friction state between tires and a road surface (state of the road surface) and the state of the tires, such as the internal pressure or the wear of the tires, can be detected with precision by measuring the quasi-electrostatic field produced by the contact between running tires and the road surface and distributed over the external surface of the tires and the vehicle body.

Thus, the measuring method according to this invention is characterized by having the steps of detecting charge potential distributed over a vehicle body or tires resulting from the contact, separation, and friction between the tires and the road surface and monitoring the amplitude of the charge potential detected in the step of detecting.

BRIEF DESCRIPTION OF THE DRAWINGS

FIG. 27 is a diagram showing the temperature dependence and frequency dependence of tan δ.

Figure 1:
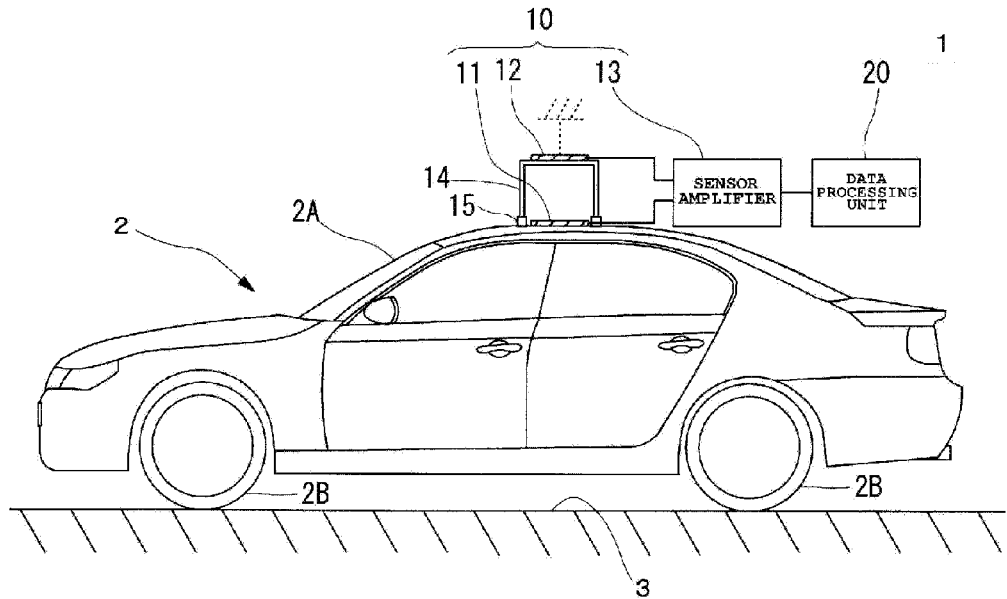
FIG. 1 is a schematic diagram showing a constitution of a measuring apparatus in accordance with the first embodiment of the present invention.

BEST MODE FOR CARRYING OUT THE INVENTION (1) Detection Principle

A description is given of the detection principle of the present invention before explaining the preferred embodiments of the invention.

The detection principle of the present invention consists in detecting the charge potential distributed over a vehicle body which results from contact, separation, and friction between the tires and the road surface as an indicator in identifying the state of the road surface.

It is a known fact that a charge potential occurs between a tire and a road surface as a result of contact, separation, and friction between the tire and the road surface, as is described in the "Description of the Related Art" of Japanese Unexamined Patent Application Publication 2011-225023.

However, to the knowledge of the inventors, there has been no conventional art for the detection of charge potentials occurring between a tire and a road surface. And the inventors believe that two main factors are contributing to this situation.

As a first factor, it has been assumed difficult to detect the charge potentials occurring between tires and a road surface directly.

As a second factor, it has been assumed impossible to detect the charge potentials occurring between tires and a road surface wet with water (hereinafter referred to as "wet road surface") because the wet road surface permits the electric charge to immediately migrate to the ground through the water.

Thus one of the challenges for the inventors was to come up with an effective methodology for detecting charge potentials occurring between tires and a road surface. In this connection, the inventors have made a discovery that even when the road surface is a wet road surface, the charge potential occurring between tires and the road surface exists in a film-like distribution over the surface of an entire vehicle body. And the inventors have succeeded in detecting the charge potential occurring between tires and a road surface resulting from contact, separation, and friction between the tires and the road surface from a space above the external surface of a vehicle body.

The charge potential that occurs between the tire and the road surface can be an indicator in directly identifying the state of the road surface since it is a parameter that varies with the road surface material or the type of objects that exist between the tire and the road surface. Therefore, a road surface covered with steel sheets and a wet road surface, for instance, which are both more slippery than a concrete road surface, can be identified according to the laws of physics. It may also be possible to widen the variation in identifying the state of the road surface if acceleration is added as another indicator in identifying the road surface condition.

Thus, charge potentials distributed over a vehicle body which result from the contact, separation, and friction between the tires and the road surface are detected according to the detection principle of the present invention. And this method can improve the accuracy of identification of the state of the road surface markedly in contrast to the cases where acceleration is applied as an indicator in identifying the road surface condition.

(2) Preferred Embodiments

First Embodiment

As shown in FIG. 1, a measuring apparatus 1 according to a first embodiment of the present invention, which is to be mounted on a vehicle 2, includes a detecting unit 10 and a data processing unit 20.

The detecting unit 10 includes a sensing electrode 11, a reference electrode 12, and a sensor amplifier 13 as main constituent elements thereof.

The sensing electrode 11 is disposed on the external surface of a vehicle body 2A, and the reference electrode 12 is disposed apart from the external surface of the vehicle body 2A with a space therebetween.

In the first embodiment, the sensing electrode 11 and the reference electrode 12 are both in the form of a flat plate of the same shape and size and are disposed in parallel with each other. Also, the sensing electrode 11 is disposed at the highest point on the external surface of the vehicle body 2A, and the reference electrode 12 is disposed within a space directly above the sensing electrode 11.

Note that the reference electrode 12 is supported by a support member 14 anchored to the vehicle 2. The lower the permittivity (dielectric constant) of the support member 14, the better, since a lower permittivity assures accurate determination of the potential between the sensing electrode 11 and the reference electrode 12. The materials exhibiting low permittivity are acrylic, urethane, and glass, for instance.

In the first embodiment, the support member 14 is a receptacle having an open face at the bottom thereof and is secured to the external surface of the vehicle body 2A via a vibration absorbing member 15. The reference electrode 12 is bonded to the external surface of the top plate of the receptacle, and the sensing electrode 11 is bonded to the external surface of the vehicle body 2A enclosed by the receptacle. It is to be noted, however, that the above-described shape and the mode of support of the support member 14 are only examples and must not be construed as limiting.

The sensor amplifier 13, which is provided with a detector element, such as an FET (Field Effect Transistor), and an amplifier, detects the potential between the sensing electrode 11 and the reference electrode 12 as the signal (hereinafter referred to as "potential signal") and amplifies the potential signal. Note that the potential between the sensing electrode 11 and the reference electrode 12 is mainly the charge potential distributed over the entirety of the vehicle body 2A which is caused between the tire 2B and the road surface 3 by the contact, separation, and friction therebetween.

As described above, the detecting unit 10 detects the charge potential distributed over the vehicle body resulting from the contact, separation, and friction between the tire 2B and the road surface 3.

The data processing unit 20, which is incorporated in the casing of an electronic unit of the vehicle 2 or in an independent casing separate from the electronic unit, is connected to the sensor amplifier 13 via a cable. Note that when the data processing unit 20 is incorporated in an independent casing separate from the electronic unit of the vehicle 2, the casing may be disposed on the external surface of the vehicle body 2A or inside the vehicle.

Figure 2A:
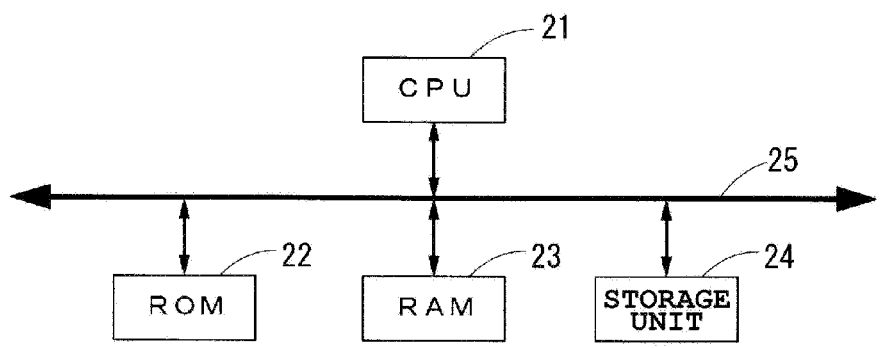
FIGS. 2(A) and 2(B) are schematic diagrams showing a constitution of a data processing unit.

As shown in FIG. 2A, the data processing unit 20 is composed of a CPU (Central Processing Unit) 21, which controls the data processing unit 20, and various other hardware connected thereto. For example, a ROM (Read Only Memory) 22, a RAM (Random Access Memory) 23, which serves as a working memory of the CPU 21, and a storage unit 24 are connected to the CPU 21 via a bus 25. Stored in the storage unit 24 is a program for measuring the charge potential caused by the contact, separation, and friction between the tire and the road surface (hereinafter referred to as "measurement program").

Figure 2B:
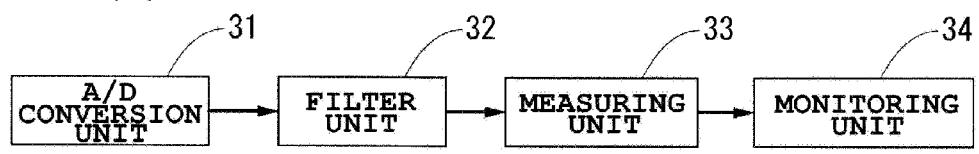

On receipt of an instruction to measure the charge potential caused by the contact, separation, and friction between the tire and the road surface, the CPU 21 develops the measurement program onto the RAM 23 and functions as an A/D conversion unit 31, a filter unit 32, a measuring unit 33, and a monitoring unit 34 as shown in FIG. 2B.

The A/D conversion unit 31 converts the potential signal outputted from the sensor amplifier 13 into the data (hereinafter referred to as "potential data"). The filter unit 32 extracts a predetermined frequency range from the potential data outputted from the A/D conversion unit 31.

The measuring unit 33 stores the potential data outputted from the filter unit 32 into the storage unit 24 and at the same time sends it out to the monitoring unit 34. It is to be noted that the measuring unit 33 may execute a predetermined data compression processing on the potential data to be stored in the storage unit 24.

Figure 3:
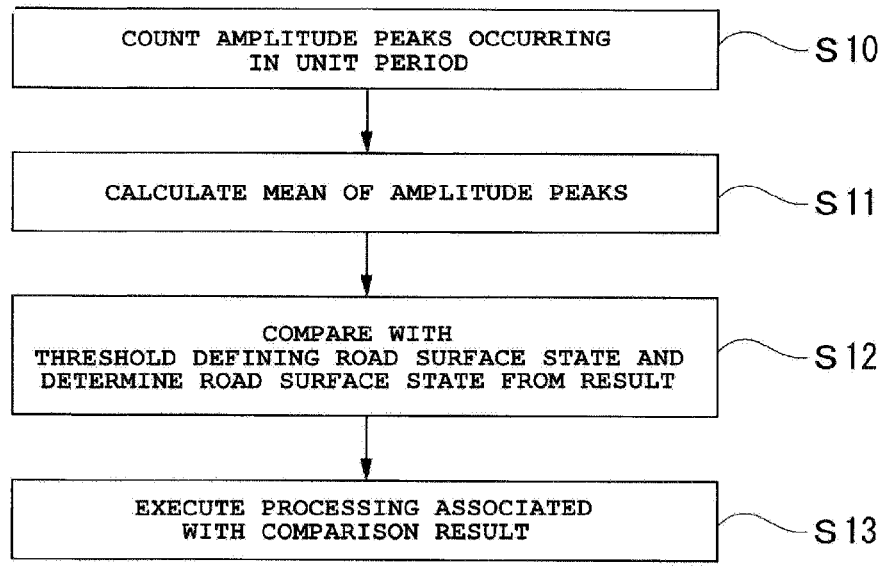
FIG. 3 is a flowchart showing a procedure of monitoring processing.

The monitoring unit 34 identifies a state of the road surface by executing a monitoring processing in accordance with the flowchart shown in FIG. 3 using the potential data outputted from the measuring unit 33. That is, upon receipt of an instruction to measure the charge potential caused by the contact, separation, and friction between the tire and the road surface, the monitoring unit 34 starts a monitoring process and goes to step S10.

In step S10, the monitoring unit 34 counts amplitude peaks occurring in a unit period on the plus or minus side relative to the reference level.

In step S11, the monitoring unit 34 calculates a mean of the amplitude peaks whenever the amplitude peaks in a unit period are counted in step S10.

In step S12, the monitoring unit 34 compares, each time the mean of the amplitude peaks is calculated in step S11, the mean against thresholds defining the states of the road surface and estimates the state of the road surface from the result of comparison.

Figure 4A:
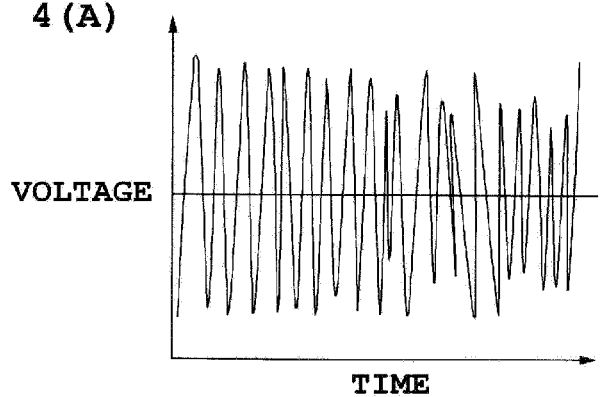
FIGS. 4(A) and 4(B) are graphs showing amplitude waveforms of charge potential distributed over a vehicle body caused by contact, separation, and friction between a tire and a road surface.
Figure 4B:
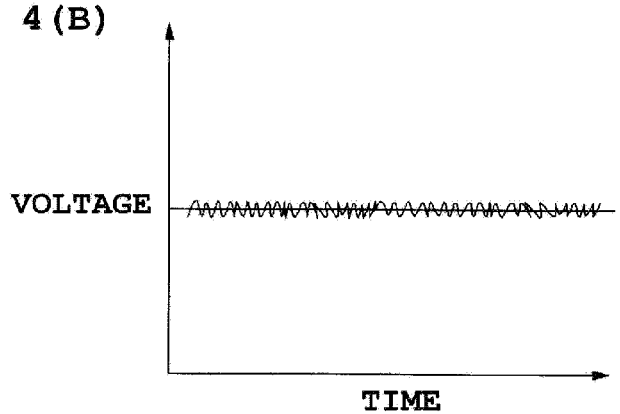

Although actual measured waveforms are not disclosed here, the waveforms of the amplitude of the charge potential distributed over a vehicle body traveling on a wet road surface and the amplitude of the charge potential distributed over a vehicle body traveling on a dry road surface are approximately as shown in FIGS. 4(A) and 4(B). As is evident in FIGS. 4(A) and 4(B), there is a significant difference between the amplitude of the charge potential distributed over a vehicle body traveling on a wet road surface (FIG. 4 (A)) and the amplitude of the charge potential distributed over a vehicle body traveling on a dry road surface (FIG. 4(B)).

To be more precise, as an experimental result shows, the mean of the amplitudes of the charge potential distributed over a vehicle body traveling at a speed of 30 km/h is 0.06 V on a wet road surface and 0.3 V on a dry road surface, representing a potential difference of about five times. Also, as an experimental result shows, the mean of the amplitudes of the charge potential distributed over a vehicle body traveling at a speed of 60 km/h is 0.09 V on a wet road surface and 0.55 V on a dry road surface, representing a potential difference of about six times. In other words, the faster the vehicle runs, the more distinct the difference between the wet road surface and the dry road surface in the amplitude difference of charge potential distributed over the vehicle body will be.

It is extremely important that these experimental results show significant amplitude differences of charge potential distributed over the vehicle body between the wet road surface and the dry road surface, because there have so far been no parameters found by which the difference is grasped to an extent that the difference between the wet road surface and the dry road surface can be identified. Therefore, it is at least possible to detect the difference between a wet road surface and a dry road surface with greater precision than in the past by monitoring the degrees of change in a unit period in the potential detected by the sensor amplifier 13.

For example, a difference of 5 times or more may be set between the upper limit of the threshold set for the identification of a wet road and the lower limit of the threshold set for the identification of a dry road with respect to the mean of the amplitudes in a unit period of the potential detected by the sensor amplifier 13. With the thresholds set like this, it is possible to detect the difference between a wet road surface and a dry road surface with greater precision than in the past when the vehicle runs at a speed of 30 km/h or above.

It should be noted that thresholds defining various states of the road surface may be set in place of those for the wet road surface and the dry road surface or in addition to those for the wet road surface. Also, as the number of these thresholds increases, it may be possible to better identify the states of the road surface corresponding to the road surface materials and the types of objects that exist between the tire and the road surface.

In step S13, the monitoring unit 34 executes a processing associated with the result of comparison in step S12. For example, when the mean of the amplitude peaks calculated in step S11 is below the upper limit of the threshold set to define a wet road surface, the monitoring unit 34 stores in the storage unit 24 a flag indicating that the part of the electronic data where the amplitude peak has occurred corresponded to a wet road surface. As another example, the monitoring unit 34 may give a warning instruction to the electronic unit in the vehicle body indicating that care should be taken for driving on a wet road surface.

Thus, the data processing unit 20 identifies the state of the road surface according to the size of amplitude of charge potential by monitoring the amplitudes of charge potential distributed over the vehicle body resulting from the contact, separation, and friction between the tire 2B and the road surface 3.

As described thus far, the measuring apparatus 1 according to the first embodiment detects the charge potential distributed over the vehicle body 2A resulting from the contact, separation, and friction between the tire 2B and the road surface 3.

Therefore, the measuring apparatus 1 can detect the charge potential caused between the tire 2B and the road surface 3 accurately without placing the detecting unit 10 between the tire 2B and the road surface 3.

Also, the measuring apparatus 1 according to the first embodiment monitors the amplitudes of the charge potential distributed over the vehicle body 2A resulting from the contact, separation, and friction between the tire 2B and the road surface 3.

As already mentioned, the charge potential caused between the tire 2B and the road surface 3 is a parameter that can vary with the material of the road surface 3 and the type of object existing between the tire 2B and the road surface 3 and as such can serve as an indicator in directly identifying the state of the road surface 3. Hence, the measuring apparatus 1 can identify the state of the road surface with accuracy according to the size of amplitudes of the charge potential.

In the foregoing first embodiment, the sensing electrode 11 is disposed on the external surface at the highest position of the vehicle body 2A. However, the position of the sensing electrode 11 is not limited to the one in this embodiment. For example, the internal surface of the vehicle body 2A may be selected as where the sensing electrode 11 is to be located. As other examples, a position on the bottom or side of the vehicle body 2A, a position on the trunk panel or rear seat door, or a position on a conductor connected to the vehicle body 2A may be selected as the location of the sensing electrode 11. In other words, the sensing electrode 11 may be disposed anywhere on the surface of the vehicle body 2A.

It is to be noted that the vehicle body 2A itself may be used as the conductor in place of the sensing electrode. However, when the vehicle body 2A itself is used as the conductor in place of the sensing electrode, the cable wired to the sensor amplifier 13 must be connected to the vehicle body 2A. In this case, the vehicle body 2A, as a rule, comes with a coating applied thereon. Hence it is necessary that the coating at the position for cable connection is left undone at the time of manufacture or removed before the cable connection. If the potential distributed over the surface of a vehicle body is to be detected without going to such a trouble, the sensing electrode 11 should preferably be disposed on the surface (coated surface) at a conductor position of the vehicle body 2A. Also, when the vehicle body 2A itself is used as the conductor in place of the sensing electrode, the sensitivity of the sensor amplifier 13 must be enhanced. To that end, it is necessary that a cable thick enough be used to widen the contact area of the cable to the surface of the metallic part of the vehicle body 2A. Hence, if a certain level of sensitivity of the sensor amplifier 13 is to be achieved without employing a thicker cable, the sensing electrode 11 should preferably be disposed on the surface (coated surface) at a conductor position of the vehicle body 2A.

Also, in the foregoing first embodiment, the reference electrode 12 is disposed in a space directly above the highest position of the vehicle body 2A. However, the position of the reference electrode 12 is not limited to the one in this embodiment. For example, a space above the internal surface of the vehicle body 2A may be selected as a space where the reference electrode 12 is located. As other examples, a position on the bottom or side of the vehicle body 2A or a space above the surface of the trunk panel or rear seat door may be selected as the location of the reference electrode 12. In other words, the reference electrode 12 may be disposed anywhere as long as it is spaced apart from the surface of the vehicle body 2A.

However, if the electrostatic coupling with objects around the vehicle or component parts of the vehicle is to be reduced, the reference electrode 12 should preferably be disposed in a position above the external surface of a vehicle body part posterior to the vertical plane passing through the border between the upper end of the windshield and the vehicle body and more preferably in a position above the external surface of the highest vehicle body position.

Figure 5:
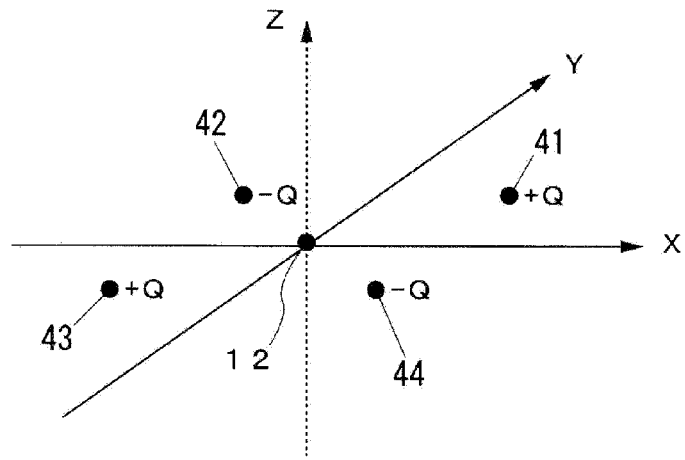
FIG. 5 is a diagram showing a quadrupole.

It is to be noted also that, as shown in FIG. 5, the reference electrode 12 may be provided with four electrodes 41 to 44 (hereinafter referred to as "quadrupole") which are arranged as the vertexes of a square with the reference electrode 12 at the median point with the neighboring vertexes being charged with inverted polarity. With this reference electrode 12 provided with the quadrupole, the electric fields occurring from the neighboring electrodes 41-42, 42-43, 43-44, and 44-41 cancel out each other irrespective of time change. Also, the intensity of the electric field created by each of the electrodes 41 to 44 is attenuated at the rate of $2^5$ ($2^{m+1}$: m being the number of electrodes) times distance, and the extent of the electric field is localized to the extreme vicinity. Therefore, the external coupling range to the electrodes 41 to 44 is localized to the extreme vicinity. As such, the intensity of electric field in the vicinity of the reference electrode 12 is 0 V/m or of a value near it. Therefore, the electrostatic coupling with the road surface 3 or the component parts of the vehicle 2 is significantly reduced even when the reference electrode 12 is disposed in a space above the internal surface of the vehicle body 2A or in a space above the external surface of a bottom position of the vehicle body 2A. As a result, the reference electrode 12 performs with great stability, and the potential between the sensing electrode 11 and the reference electrode 12 can be detected with markedly improved accuracy. Thus, when a quadrupole is used, the potential between the sensing electrode 11 and the reference electrode 12 can be detected with markedly improved accuracy irrespective of the position of the reference electrode 12 on the surface of the vehicle body 2A. Note, however, that the electrode structure like this is not limited to the above-described quadrupole. That is, the structure usable may consist of 2n pieces of electrodes which are arranged as the vertexes of a regular polygon with 2n sides (n being 2 or an even number greater than 2) with the neighboring vertexes being charged with inverted polarity. If the distance from the median point of the regular polygon with 2n sides to each vertex is constant, then the greater n is, the shorter the distance between the neighboring charges (the length of the sides of the polygon) will be, thus improving the efficiency with which the electric fields created by the electrodes cancel out each other. Therefore, it is possible to further stabilize the performance of the reference electrode 12 by selecting an electrode structure with a greater value of n. For further information on the electrode structure like this, refer to Japanese Patent Application NO. 2007-56954 disclosed by the same inventors.

When the electrode structure as described above is not used, it is advisable that the reference electrode 12 is disposed apart from the external surface of the vehicle body 2A with a space of 7.5 μm or more therebetween. The value of 7.5 μm has been obtained from a simulation, which is described below.

<Method of the Simulation>

Figure 6:
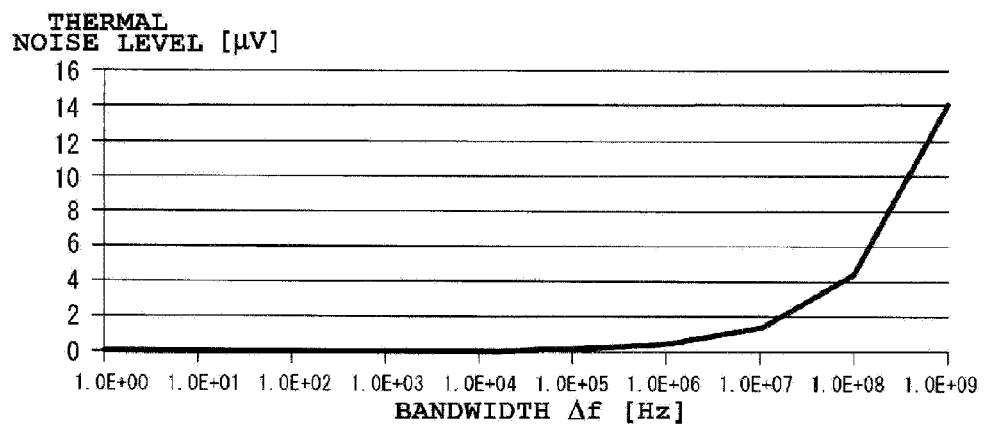
FIG. 6 is a graph showing a relationship between thermal noise level and frequency.

The potential occurring at the external surface of a vehicle running on a wet road surface is assumed to be 0.1 V. The values of the thermal noise level occurring at the sensor amplifier are assumed to be the values as shown in FIG. 6. And the distance at which the potential difference from the surface of the vehicle body 2A to the reference electrode 12 is at or above the thermal noise level is obtained.

The value of 0.1 V is the average of the actual measurements obtained in an experiment in which a sedan carrying a sensing electrode on the external surface of a roof position of the vehicle body and a reference electrode within a space directly above the sensing electrode is operated on a surface wetted with water of a test running course.

FIG. 6 shows the thermal noise levels within the frequency range of 1 Hz to 1 GHz calculated by means of a general formula representing the level of thermal noise. According to the general formula, the level P (dbm) of thermal noise at 26.85° C. is P=−174+10 log (Δf) where f is the frequency.

<Conditions for the Simulation>

The simulator used is Version 2.0 of EEM-STF of Information and Mathematical Sci. Lab. The vehicle body is assumed to be a 1 m×1 m electrode, to which the above-mentioned 0.1 V is applied. On the other hand, the reference electrode is assumed to be a 1 m×1 m infinite distance electrode, to which 0 V is applied. Also, the distance between the electrode which is assumed to be the vehicle body and the electrode which is assumed to be the reference electrode is set at 1 m.

<Results of the Simulation>

Figure 7:
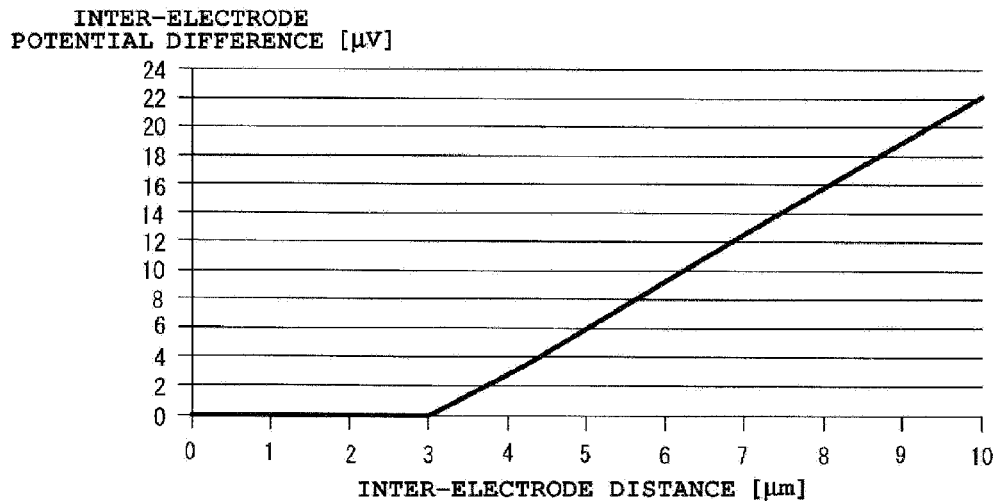
FIG. 7 is a graph showing a relationship between interelectrode distance and interelectrode potential difference based on a simulation.

FIG. 7 shows a relationship between the inter-electrode distance and the inter-electrode potential difference derived from the simulation as described above. The maximum value of the thermal noise level in the frequency range between 1 Hz and 1 GHz is 14.1 μV as shown in FIG. 6, and the inter-electrode distance that can realize the potential difference equal to or above 14.1 μV is 7.5 μm as shown in FIG. 7. As already mentioned, the amplitude of charge potential distributed over a vehicle body traveling on a wet road surface is about one fifth of that on a dry road surface. Therefore, when the reference electrode 12 is disposed apart from the external surface of the vehicle body 2A with a space of 7.5 μm or more without using the above-described electrode structure therefor, potentials equal to or above the potential occurring on the external surface of the vehicle body traveling on a wet road surface can be detected within the frequency range from 1 Hz to 1 GHz.

Also, in the foregoing first embodiment, the reference electrode 12 is disposed in a space directly above the sensing electrode 11. However, the reference electrode 12 may be disposed elsewhere than in a space directly above the sensing electrode 11. It is to be noted, however, that when the vehicle body 2A has a sun roof or the like made of glass or acrylic, which is a low dielectric material, the reference electrode 12 should preferably be disposed in a space directly above the low dielectric material. Disposed as such, the electrostatic coupling between the reference electrode 12 and the vehicle body 2A is reduced further than when there is a metallic part of the vehicle body 2A directly below the reference electrode 12. As a result, the reference electrode 12 performs with marked stability, and the potential between the sensing electrode 11 and the reference electrode 12 can be detected with markedly improved accuracy.

Also, in the foregoing first embodiment, the sensing electrode 11 and the reference electrode 12 are both flat plates of the same shape and size. However, the sensing electrode 11 and the reference electrode 12 may be of different shapes from each other or of different sizes from each other. Also, the shape of the sensing electrode 11 and the reference electrode 12 is not limited to a flat plate, but a selection can be made from various shapes therefor.

Also, in the foregoing first embodiment, the measuring unit 33 is placed posterior to the filter unit 32, and the monitoring unit 34 posterior to the measuring unit 33. However, the arrangement may be such that the monitoring unit 34 is placed posterior to the filter unit 32, and the measuring unit 33 posterior to the monitoring unit 34. Note that the measuring unit 33 may cause part of the potential data to be stored in the storage unit 24 instead of the whole of the potential data. Also, the filter unit 32 or the monitoring unit 34 may be eliminated. Furthermore, when the data processing unit 20 is mounted on the vehicle 2, the detecting unit 10 may be mounted on the vehicle 2 as a detecting device.

Second Embodiment

The measuring apparatus 1 according to the first embodiment estimates whether the road surface is a wet road surface or a dry road surface from the mean of the amplitudes in a unit period of the charge potential detected by the detecting unit 10. However, the state of a road surface may be estimated by extracting a time-varying waveform of charge potential in each unit period and using plural pieces of the extracted time-varying waveform data. By doing so, the accuracy of estimation of a road surface condition can be further improved.

Figure 8:
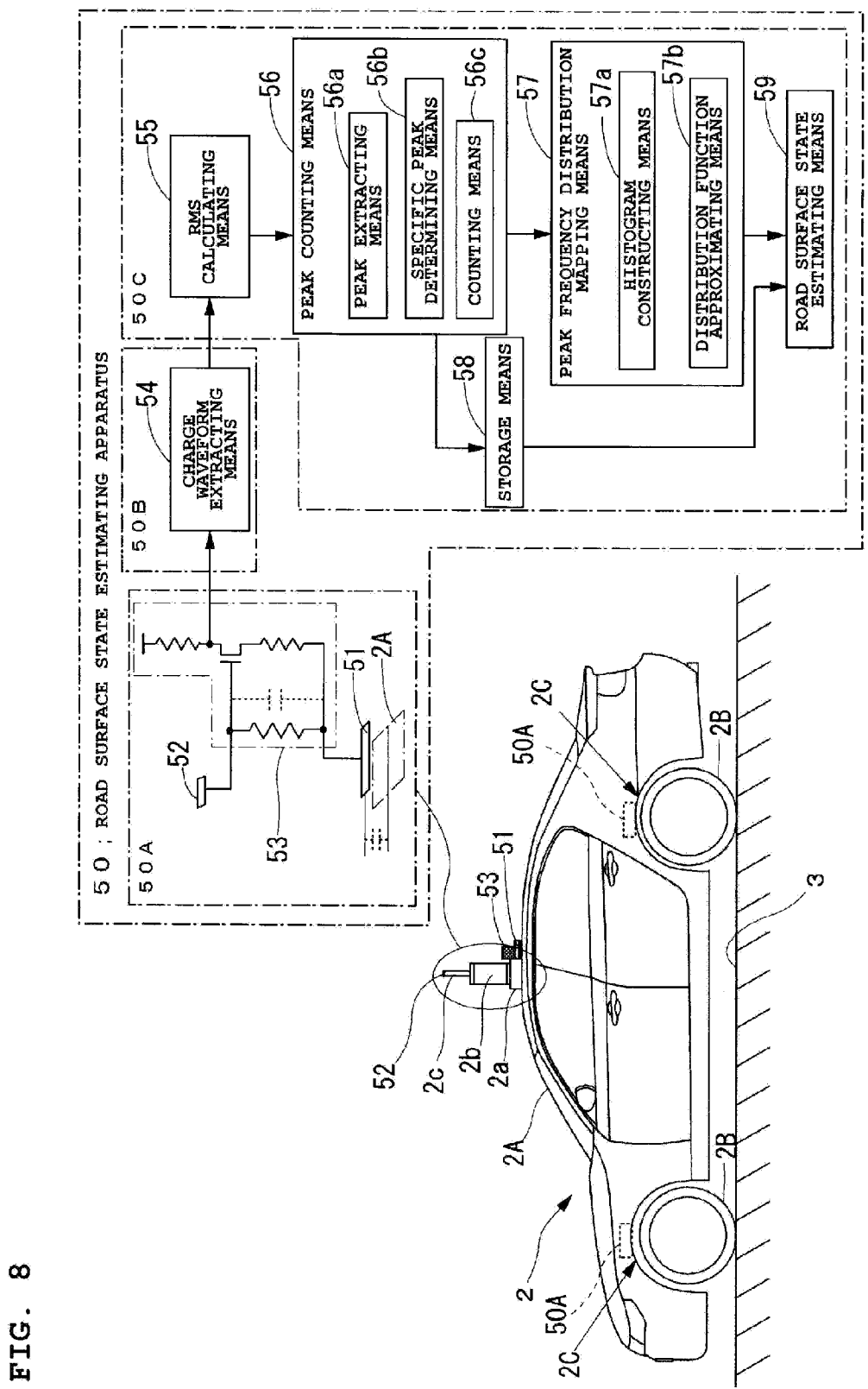
FIG. 8 is a schematic diagram showing a constitution of a road surface state estimating apparatus in accordance with the second embodiment of the present invention.

FIG. 8 is a diagram showing a constitution of a road surface state estimating apparatus 50 according to a second embodiment of the present invention. The road surface state estimating apparatus 50 includes a sensing electrode 51, a reference electrode 52, a sensor amplifier 53, a charge waveform extracting means 54, an RMS (Root Mean Square) calculating means 55, a peak counting means 56, a peak frequency distribution mapping means 57, a storage means 58, and a road surface state estimating means 59.

The means from the sensing electrode 51 to the sensor amplifier 53 constitute a detecting unit 50A that detects the charge potential caused by the contact, separation, and friction between the tire and the road surface; the charge waveform extracting means 44 constitutes a monitoring unit 50B that monitors the charge potential detected by the detecting unit 50A; and the means from the RMS calculating means 55 to the road surface state estimating means 59 constitute an estimating unit 50C.

As with the data processing unit 20 of the first embodiment, the monitoring unit 50B and the estimating unit 50C are constituted by a storage unit, such as ROM and RAM, and a microcomputer program.

The sensing electrode 51, which is a plate electrode, is disposed apart from the external surface of the vehicle body 2A with an air gap therebetween and capacitive-coupled to the vehicle body 2A. In this embodiment, a dielectric plate of constant thickness is inserted in the air gap between the external surface of the vehicle body 2A and the sensing electrode 51 so as to increase a capacitance between the sensing electrode 51 and the vehicle body 2A, and secure the size of the air gap.

On the other hand, the reference electrode 52, which is also a plate electrode, is attached to the end of a support post 2c made of a resin, such as acrylic or urethane, attached to project from the upper end of a support stand 2b on a vibration-absorbing pedestal 2a secured to the external surface of the vehicle body 2A. The support stand 2b is a cylindrical member which has an insulating member, such as a wooden plate, attached to the vibration-absorbing pedestal 2a side and the support post 2c side thereof.

This will not only separate the reference electrode 52 far enough from the charged vehicle body 2A (e.g., 100 mm or more), but also electrically insulate the reference electrode 52 and the vehicle body 2A from each other. As a result, the reference electrode 52 may be maintained at zero potential constantly.

The charge potential on the vehicle body 2A fluctuates to the (+) side and the (−) side cyclically. Accordingly, the potential at the sensing electrode 51, which is capacitively coupled to the vehicle body 2A, fluctuates between the plus side and the minus side with time.

Also, the charge potential on the vehicle body 2A changes with the changes in the capacitance between the tire 2B and the road surface 3. And the capacitance between the tire 2B and the road surface 3 changes with the state of the road surface. Therefore, the changes in the state of the road surface can be detected by detecting the changes in the above-mentioned charge potential.

The sensor amplifier 53, which is, for example, an FET (Field Effect Transistor) amplifier, amplifies the voltage between the sensing electrode 51 and the reference electrode 52 (hereinafter referred to as "charged voltage") before outputting it.

The charge waveform extracting means 54 extracts the charge waveform, which is the time-varying waveform of the charged voltage for each revolution of the tire, sequentially from the time-varying waveform of the charged voltage amplified and continuously outputted by the sensor amplifier 53.

Figure 9A:
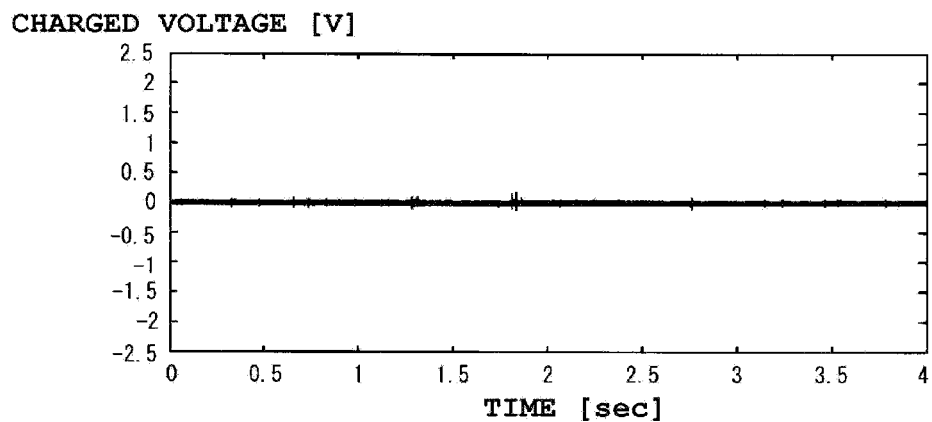
FIGS. 9(A) and 9(B) are diagrams showing examples of time-varying waveforms of charged voltage.
Figure 9B:
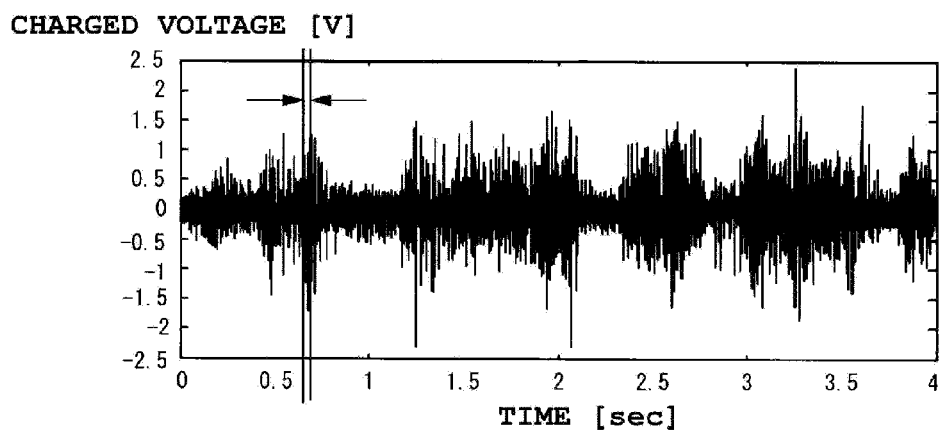

FIGS. 9 (A) and 9 (B) show examples of time-varying waveforms of the charged voltage. FIG. 9 (A) shows a time-varying waveform of a vehicle at a stop on a dry road surface. FIG. 9 (B) shows a time-varying waveform of a vehicle running on a dry road surface.

As is clear from the comparison between the time-varying waveforms of a vehicle at a stop and a vehicle running, the amplitude of the time-varying waveform of a running vehicle is not necessarily constant. This is due to the changes in the mode of contact of the tire with the moisture on the road surface, which can be influenced by the unevenness or the like of the road surface.

In the second embodiment, the unit period is set at one revolution of the tire, and the state of the road surface is estimated using the data of charge waveforms of N revolutions of the tire sequentially extracted by the charge waveform extracting means 54.

The RMS calculating means 55 calculates an RMS value of extracted charge waveform for each revolution of the tire and stores it in the storage means 58.

The peak counting means 56, which includes a peak extracting means 56a, a specific peak determining means 56b, and a counting means 56c, counts the number of specific peaks in a charge waveform. The specific peaks will be discussed later.

The peak extracting means 56a extracts peaks on the (+) side and peaks on the (−) side of the charge waveform.

The specific peak determining means 56b calculates a peak value difference which is the difference between the amplitude value of a peak on the (+) side and the amplitude value of a temporally adjacent peak on the (−) side and compares the peak value difference against the RMS value stored in the storage means 58. And when the peak value difference is larger than the RMS value, the specific peak determining means 56b determines the temporally posterior peak as a specific peak.

The RMS value varies with the unevenness of the road surface or the speed of the vehicle. Therefore, as in this embodiment, it is possible to eliminate unnecessary peaks more reliably if the peaks whose peak value difference is larger than the RMS value are determined as specific peaks than if a threshold is set for the amplitude value difference and the peaks whose amplitude value difference is larger than the threshold are determined as specific peaks.

Figure 10:
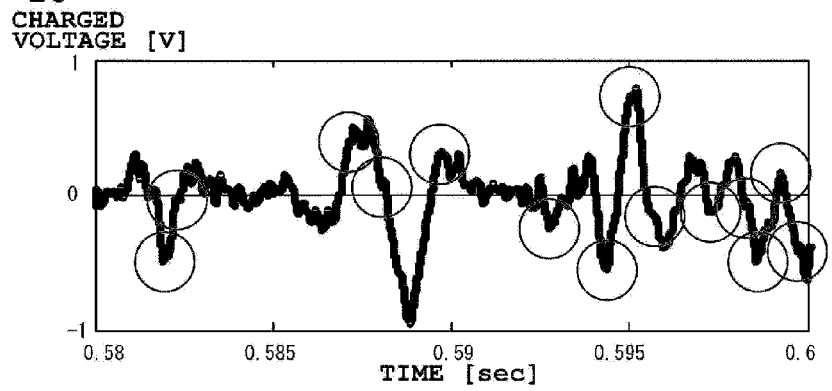
FIG. 10 is an enlarged illustration of a time-varying waveform of charged voltage.

FIG. 10 is a closeup of FIG. 9 (B), in which circled peaks are specific peaks.

The counting means 56c counts the number of occurrences of specific peaks. The number of occurrences is counted for each revolution of the tire, and the results of counting are stored in the storage means 58. The counting of the number of occurrences is done N times, which is the predetermined number of times, or for the N units of charge waveforms.

The peak frequency distribution mapping means 57 includes a histogram constructing means 57a and a distribution function approximating means 57b.

The histogram constructing means 57a constructs a histogram representing a frequency distribution of the numbers of specific peak occurrences, using the data on the number of specific peak occurrences for each revolution of the tire stored in the storage means 58.

Figure 11:
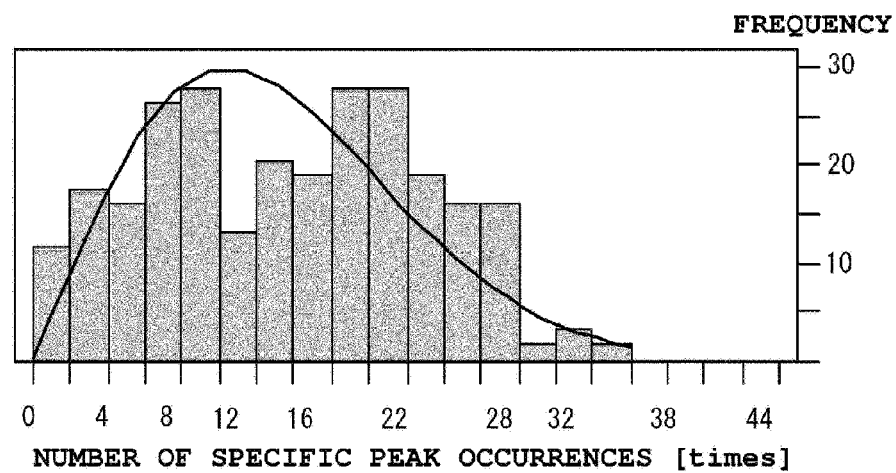
FIG. 11 is a diagram showing an example of a histogram showing a frequency distribution of the numbers of specific peak occurrences.

FIG. 11 shows an example of a histogram, of which the horizontal axis is the number of occurrences of specific peaks and the vertical axis the frequency.

When the vehicle runs on a wet road surface, the amplitude of the charge waveform is small. Accordingly, the frequency distribution is expected to have higher frequencies of smaller numbers of specific peak occurrences and lower frequencies of larger numbers of specific peak occurrences. On the other hand, when the vehicle runs on a dry road surface, the specific peaks occur with greater certainty. Accordingly, the frequency distribution is expected to have higher frequencies within a range of a certain width centered around a certain number of specific peak occurrences.

The distribution function approximating means 57b approximates, by a Weibull distribution which is mainly used to statistically represent failure phenomena of objects, the histogram representing a frequency distribution of the numbers of specific peak occurrences constructed by the histogram constructing means 57a and calculates the scale parameter n and the shape parameter m of the probability density function of the Weibull distribution given by equation (2) below.

$$f(X) = \frac{m}{\eta}\left(\frac{X}{\eta}\right)^{m-1} \exp\left\{-\left(\frac{X}{\eta}\right)^m\right\}$$ [Equation 2]

Figure 12A:
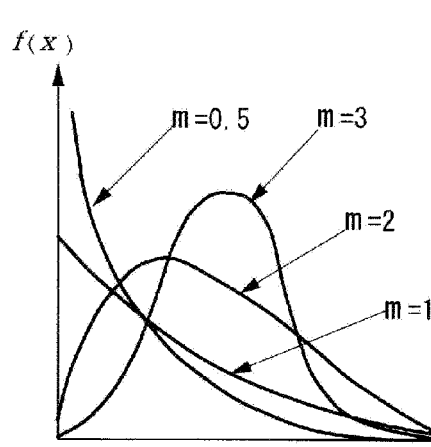
FIGS. 12(A) and 12(B) are diagrams showing probability density functions of Weibull distributions.

The shape parameter m of the probability density function of a Weibull distribution is the parameter appertaining to the shape of distribution. As shown in FIG. 12 (A), when m is small, f(x) has no peak and decreases rapidly with the increase of x. And when m is large, f(x) has a peak.

The scale parameter $\eta$ is the parameter appertaining to the position and height of the peak. As shown in FIG. 12 (B), when $\eta$ is small, the position coordinate of the peak is small and the height is high. And when $\eta$ is large, the position coordinate of the peak is large and the height is low.

That is, on a wet road surface, for which the frequency distribution is expected to have higher frequencies of smaller numbers of specific peak occurrences and lower frequencies of larger numbers of specific peak occurrences, the shape parameter m when the frequency distribution is approximated by the probability density function of a Weibull distribution is expected to be small. And on a dry road surface, for which the specific peaks occur with greater certainty, the shape parameter m is expected to be large.

In the present embodiment, the state of the road surface is estimated by the use of the shape parameter m as will be discussed later.

The storage means 58 stores not only the RMS value of the charge waveform for each revolution of the tire extracted by the RMS calculating means 55 and the number of specific peak occurrences for each revolution of the tire counted by the counting means 56c as already mentioned, but also a map representing a relationship between the state of the road surface and the shape parameter m. In the present embodiment, a reference shape parameter $m_0$ is stored as the threshold for the identification of a dry road surface or a wet road surface.

The map representing a relationship between the state of the road surface and the shape parameter m can be constructed using the data of the histogram representing a frequency distribution of the numbers of specific peak occurrences which have been obtained by operating a vehicle carrying the road surface state estimating apparatus 50 according to the second embodiment on various road surfaces including dry road surfaces and wet road surfaces. The reference shape parameter $m_0$ is set based on this map.

It is to be noted that a plurality of the shape parameter m for the wet road surface should preferably be obtained according to the thickness of water film.

The road surface state estimating means 59 estimates whether the road surface under the running vehicle is a dry road surface or a wet road surface by comparing the shape parameter m of the probability density function of a Weibull distribution obtained by the peak frequency distribution mapping means 57 against the reference shape parameter $m_0$ stored in the storage means 58.

Figure 13A:
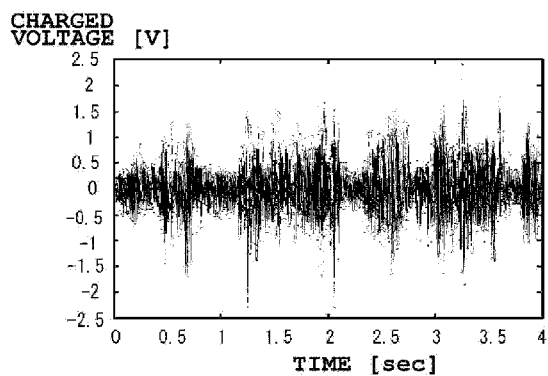
FIGS. 13(A) and 13(B) are a time-varying waveform of charged voltage and a histogram showing a frequency distribution of the numbers of specific peak occurrences during vehicular travel on a dry road surface.
Figure 13B:
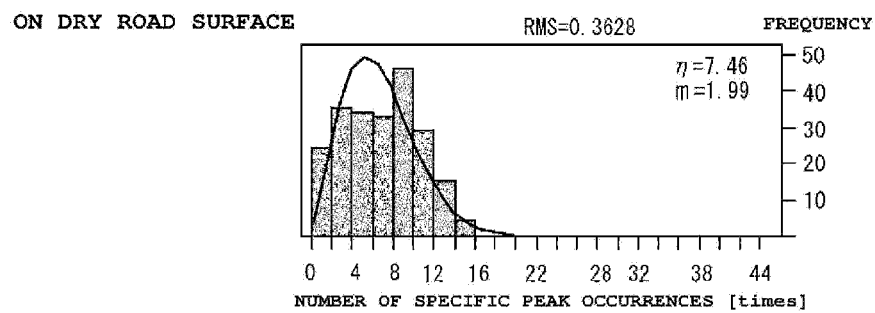
Figure 14A:
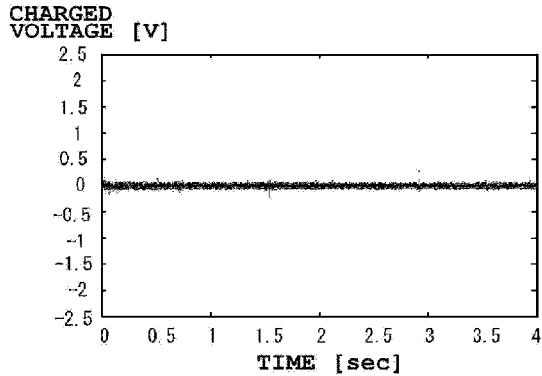
FIGS. 14(A) and 14(B) are a time-varying waveform of charged voltage and a histogram showing a frequency distribution of the numbers of specific peak occurrences during vehicular travel on a wet road surface.
Figure 14B:
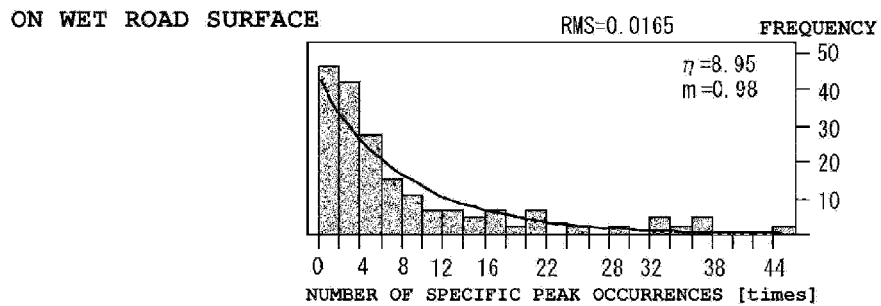

FIGS. 13 (A) and 13 (B) are a time-varying waveform of charged voltage and a histogram representing a frequency distribution of the numbers of specific peak occurrences of a vehicle running on a dry road surface. FIGS. 14 (A) and 14 (B) are a time-varying waveform of charged voltage and a histogram representing a frequency distribution of the numbers of specific peak occurrences of a vehicle running on a wet road surface.

Approximation of the histogram for the dry road surface and the histogram for the wet road surface by Weibull distributions shown by thick lines in their respective figures gives a large shape parameter m (m=1.99) of the probability density function for the dry road surface and a small shape parameter m (m=0.98) for the dry road surface.

Hence, by setting the shape parameter m as the threshold for the identification of a dry road surface or a wet road surface, it is possible to estimate the state of the road surface during vehicular travel.

That is, the road surface is estimated to be a dry road surface if $m \geq m_0$ or a wet road surface if $m < m_0$.

Also, the arrangement may be such that two thresholds $m_1$ and $m_2$ are set as $m_1 > m_0 > m_2$, and the road surface is estimated to be a dry road surface if $m \geq m_1$ or a wet road surface if $m \leq m_2$, or an instruction is given for once more of measurement if $m_1 > m > m_2$.

Figure 15:
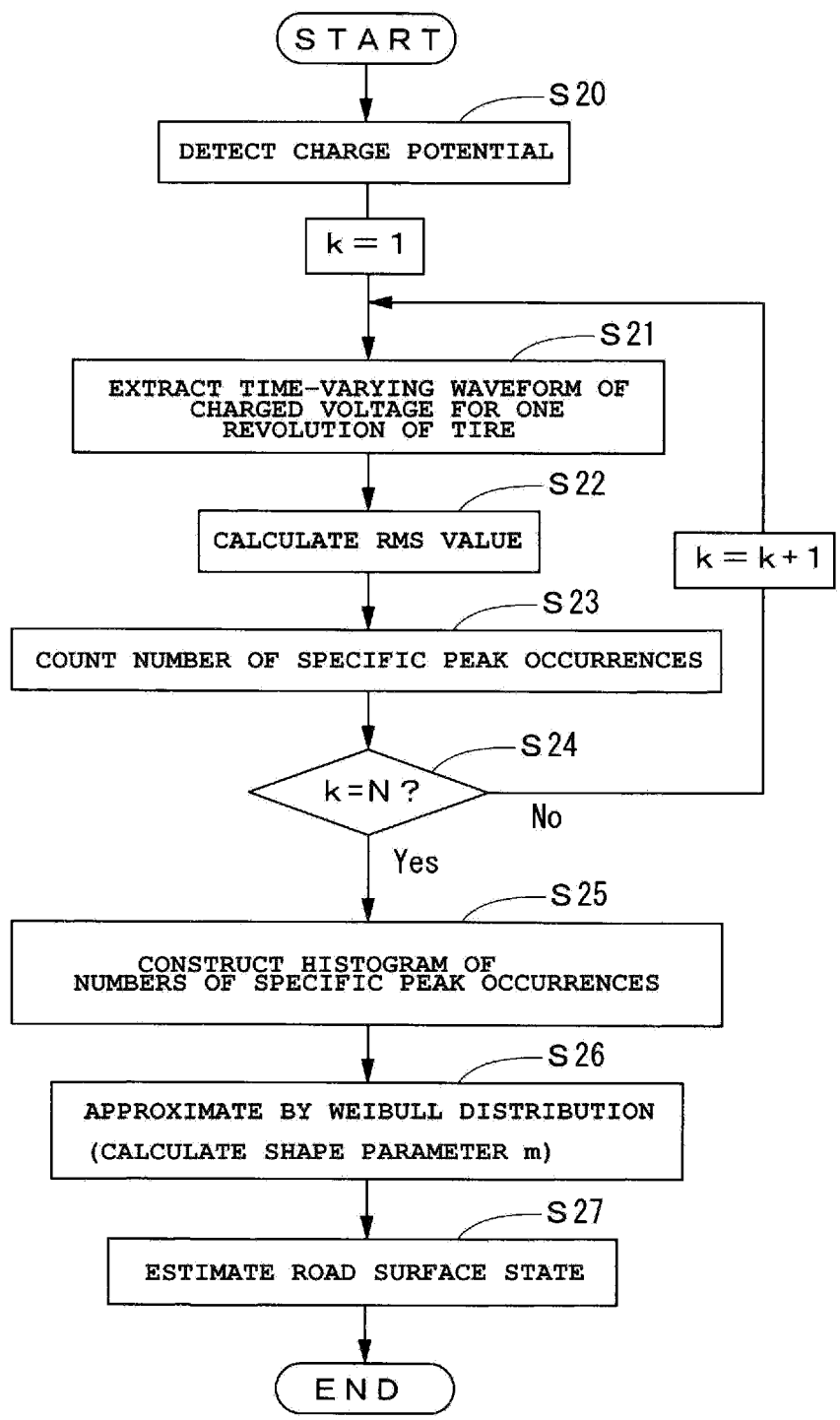
FIG. 15 is a flowchart showing a method for estimating the state of the road surface.

Next, a description is given of a method for estimating the state of a road surface during vehicular travel using the road surface state estimating apparatus 50, with reference to the flowchart of FIG. 15.

First the changes in the charge potential over the vehicle body 2A changing with the changes in the capacitance between the tire 2B of the running vehicle and the road surface 3 are detected as a time-varying waveform of charged voltage by the sensing electrode 51 capacitively coupled to the vehicle body 2A (step S20). Then a charge waveform, which is a time-series waveform of charged voltage for each revolution of the tire, is sequentially extracted from the time-varying waveform of charged voltage (step S21).

Next, the RMS value of the extracted charge waveform is calculated (step S22), and at the same time the number of specific peak occurrences, which is the number of specific peaks in the charge waveform for one revolution of the tire, is counted (step S23).

Then it is determined whether the counting of specific peak occurrences for N revolutions of the tire has been completed or not (step S24)

If the counting for N revolutions of the tire has not been completed, the procedure goes back to step S21, and the next charge waveform is extracted and the operation of counting the number of specific peak occurrences is continued.

After the counting for N revolutions of the tire is completed, a histogram representing a frequency distribution of the numbers of specific peak occurrences is constructed (step S25) and then the histogram is approximated by a Weibull distribution to calculate the shape parameter m of the probability density function of the Weibull distribution (step S26).

Finally, the road surface under the running vehicle is estimated to be a dry road surface or a wet road surface by comparing the shape parameter m against the reference shape parameter $m_0$ which is the threshold for the identification of a dry road surface or a wet road surface (step S27).

As shown in FIG. 13 (B) and FIG. 14 (B), the shape parameter $m_D$ of the probability density function when the histogram for a dry road surface is approximated by a Weibull distribution is larger than the hape parameter $m_W$ of the probability density function when the histogram for a wet road surface is approximated by a Weibull distribution. Therefore, by setting the reference shape parameter $m_0$ as $m_0=1.5$, for instance, the road surface under a running vehicle can be estimated to be a dry road surface or a wet road surface reliably.

As described above, in the second embodiment, the amplitude of the charge potential distributed over a vehicle body resulting from the contact, separation, and friction between the tire and the road surface is monitored, and the state of the road surface is detected from the time-varying waveform changing with the changes in the state of the road surface. Therefore, the state of the road surface can be detected with accuracy without installing a sensor on the tire.

In doing so, a histogram representing a frequency distribution of the numbers of specific peak occurrences is constructed from the time-varying waveform of the charged voltage; the shape parameter m of the probability density function of a Weibull distribution is obtained; and the state of the road surface is estimated using this shape parameter m. As a result, the accuracy of estimation of a road surface condition may be further improved by eliminating the influence of the unevenness of the road surface or the speed of the vehicle.

Also, in the foregoing second embodiment, the sensing electrode 51 is capacitively coupled to the vehicle body 2A as it is disposed apart from the external surface of the vehicle body 2A with an air gap therebetween. However, as with the first embodiment, the sensing electrode 51 may be disposed directly on the external surface of the vehicle body 2A.

Also, if the reference electrode 52 is placed at the median point of a quadrupole as shown in FIG. 5, then the reference electrode 52 may be disposed not only on the external surface of the vehicle body 2A but also on the internal surface thereof, and besides the performance of the reference electrode 52 may be further stabilized.

Also, in the foregoing second embodiment, a combined charge potential of four tires 2B is detected by detecting the changes in the charge potential on the vehicle body 2A. However, the sensing electrode 51 may be installed in the tire house 2C (see FIG. 8) of each tire 2B, for instance, and the road surface state may be estimated by detecting the changes in the charge potential on each tire 2B. In this manner, the accuracy of estimation of a road surface condition may be further improved.

Figure 12B:
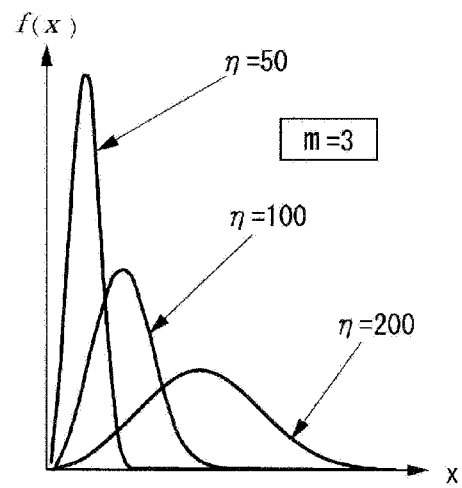

Also, in the foregoing second embodiment, the state of the road surface is estimated using the shape parameter m. However, the state of the road surface may be estimated using the scale parameter η and the shape parameter m. The scale parameter η is the parameter appertaining to the position and height of the peak. As shown in FIG. 12B, when η is small, the position coordinate of the peak is small and the height is high. And when η is large, the position coordinate of the peak is large and the height is low.

The scale parameter η is used for the estimation of the variation in the road surface under the running vehicle. That is, when η is small, frequencies of smaller numbers of specific peak occurrences are high, and when η is large, frequencies of larger numbers of specific peak occurrences are high. Therefore, the road surface can be expected to be a wet road surface when η is small or a dry road surface when η is large.

Therefore, the accuracy of estimation of a road surface condition can be further improved if the state of the road surface is estimated using both the shape parameter m and the scale parameter η.

Third Embodiment

Figure 16:
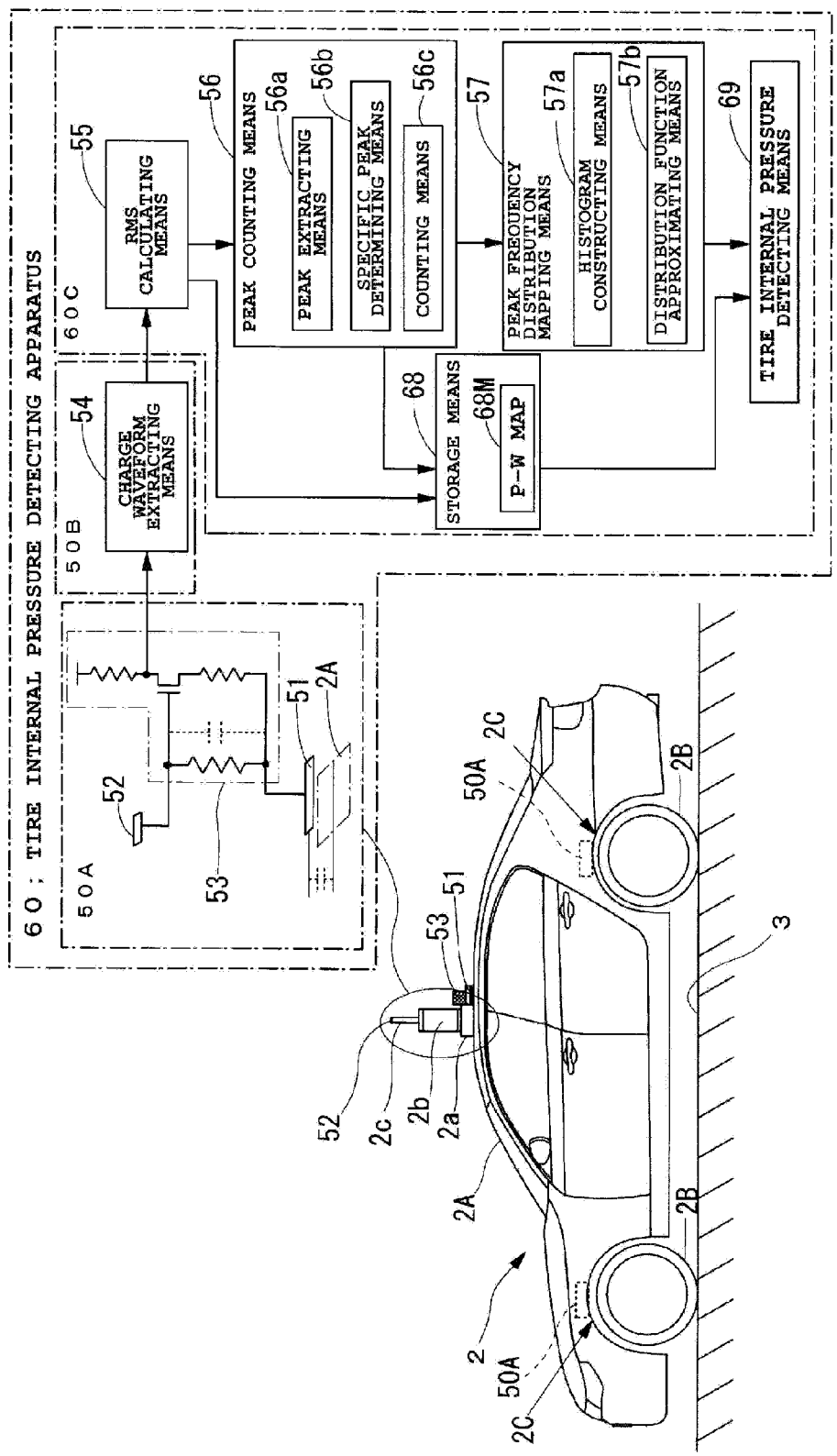
FIG. 16 is a schematic diagram showing a constitution of a tire internal pressure detecting apparatus in accordance with the third embodiment of the present invention.

FIG. 16 is a diagram showing a constitution of a tire pressure detecting apparatus 60 according to a third embodiment.

The tire pressure detecting apparatus 60 includes a sensing electrode 51, a reference electrode 52, a sensor amplifier 53, a charge waveform extracting means 54, an RMS (Root Mean Square) calculating means 55, a peak counting means 56, a peak frequency distribution mapping means 57, a storage means 68, and a tire pressure detecting means 69.

The sensing electrode 51 and the respective means from the reference electrode 52 through the peak frequency distribution mapping means 57 are of the same structure as those of the second embodiment, and so the description thereof will be omitted.

The charge potential over the vehicle body 2A changes with the changes in the capacitance between the tire 2B and the road surface 3. And the capacitance between the tire 2B and the road surface 3 also changes with the strength of the frictional force occurring between the tire and the road surface. Since the frictional force changes not only with the condition of the road surface but also with the internal pressure of the tire, the internal pressure of the tire can be detected by detecting the changes in the charge potential.

That is, the shape parameter m and the scale parameter η of the probability density function of a Weibull distribution obtained by the peak frequency distribution mapping means 57 undergo changes with the internal pressure of the tire. More specifically, when the internal pressure of the tire is low, the scale parameter η and the shape parameter m when a frequency distribution is approximated by the probability density function of a Weibull distribution are small. And when the internal pressure of the tire is high, the scale parameter η and the shape parameter m are large.

In the present embodiment, the storage means 68 stores not only the RMS value of the charge waveform for each revolution of the tire extracted by the RMS calculating means 55 and the number of specific peak occurrences for each revolution of the tire counted by the counting means 56c, but also a P-W map 68M representing a relationship between the internal pressure of the tire and the scale parameter η and the shape parameter m.

The P-W map 68M can be prepared by first constructing histograms representing the frequency distributions of numbers of specific peak occurrences which have been obtained by operating a test vehicle fitted with tires having different internal pressures and then obtaining the scale parameter η and the shape parameter m by approximating each of the histograms constructed for the different internal pressures of the tire by the probability density function of a Weibull distribution.

As the P-W map 68M, for example, a curved surface P (η, m) whose x-axis is the scale parameter η, y-axis the shape parameter m, and z-axis the internal pressure of the tire or a table listing data on the internal pressure of the tire in each of the domains of the scale parameter η [η−Δη/2, η+Δη/2] and the shape parameter m [m−Δm/2, m+Δm/2] can be used.

The tire pressure detecting means 69 detects the internal pressure of the tire by comparing the scale parameter η and the shape parameter m of the probability density function of a Weibull distribution obtained by the peak frequency distribution mapping means 57 with the P-W map 68M stored in the storage means 68.

Figure 17A:
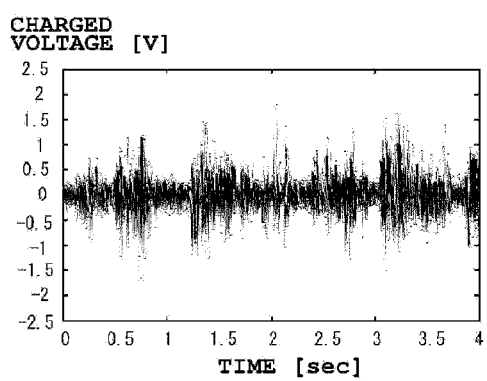
FIGS. 17(A) and 17(B) are a time-varying waveform of charged voltage and a histogram showing a frequency distribution of the numbers of specific peak occurrences when the internal pressure of the tire is low.
Figure 17B:
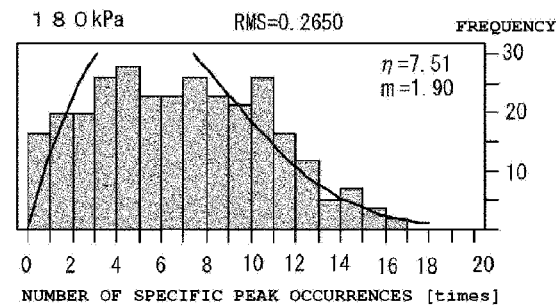
Figure 18A:
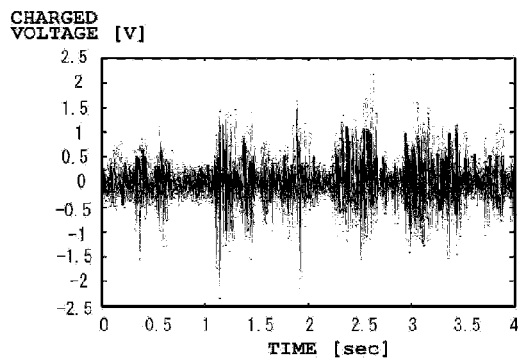
FIGS. 18(A) and 18(B) are a time-varying waveform of charged voltage and a histogram showing a frequency distribution of the numbers of specific peak occurrences when the internal pressure of the tire is high.
Figure 18B:
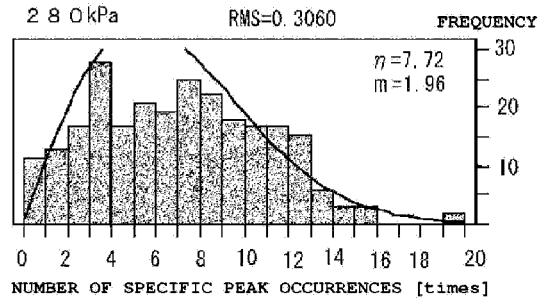

FIGS. 17A and 17B are a time-varying waveform of charged voltage and a histogram showing a frequency distribution of the numbers of specific peak occurrences, respectively, when the internal pressure of the tire is lower than the reference level of 230 kPa (180 kPa). FIGS. 18A and 18B are a time-varying waveform of charged voltage and a histogram showing a frequency distribution of the numbers of specific peak occurrences, respectively, when the internal pressure of the tire is higher than the reference level (280 kPa).

On comparison of the scale parameter η and the shape parameter m of the probability density function by approximating the histogram when the internal pressure of the tire is low and the histogram when the internal pressure of the tire is high by Weibull distributions shown by thick curves in their respective figures, it is found that the scale parameter η and the shape parameter m of the probability density function are smaller when the internal pressure of the tire is low (η=7.51, m=1.90) and the scale parameter η and the shape parameter m are larger when the internal pressure of the tire is high (η=7.72, m=1.96).

Therefore, the internal pressure of the tire can be detected with accuracy by comparing the scale parameter η and the shape parameter m with the P-W map 68M stored in the storage means 68.

That is, if the scale parameter and the shape parameter of the probability density function of a Weibull distribution obtained by the peak frequency distribution mapping means 17 are denoted by $\eta_k$ and $m_k$, respectively, the internal pressure of the tire is detected as $P_k$ when $\eta_k + \Delta\eta/2 \geq \eta \geq \eta_k + \Delta\eta/2$ and also $m_k + \Delta m/2 \geq m \geq m_k + \Delta m/2$. Here, $P_k$ is the internal pressure of the tire when the scale parameter as listed in the P-W map 68M is $\eta_k$ and the shape parameter $m_k$.

Figure 19:
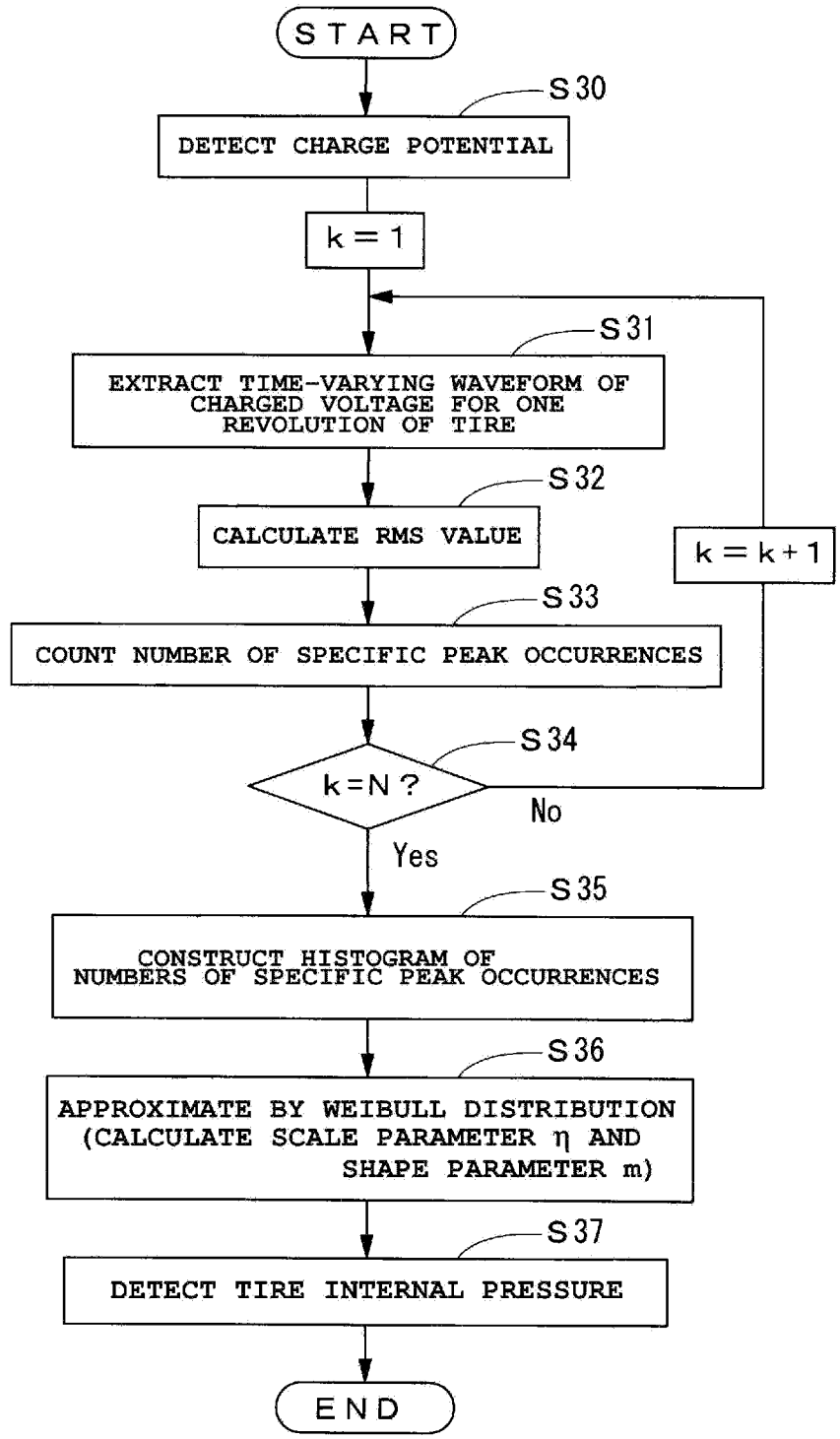
FIG. 19 is a flowchart showing a method for detecting the internal pressure of the tire.

Next, a description is given of a method for detecting the internal pressure of the tire using the tire pressure detecting apparatus 60, with reference to the flowchart of FIG. 19.

First the changes in the charge potential over the vehicle body 2A changing with the changes in the capacitance between the tire 2B of a running vehicle and the road surface 3 are detected as a time-varying waveform of charged voltage by the sensing electrode 51 capacitively coupled to the vehicle body 2A (step S30). Then a charge waveform, which is a time-varying waveform of charged voltage for each revolution of the tire, is sequentially extracted from the time-varying waveform of charged voltage (step S31).

Next, the RMS value of the extracted charge waveform for one revolution of the tire is calculated (step S32), and at the same time the number of specific peak occurrences, which is the number of specific peaks in the charge waveform for the one revolution of the tire, is counted (step S33).

Then it is determined whether the counting of specific peak occurrences for N revolutions of the tire has been completed or not (step S34)

If the counting for N revolutions of the tire is not completed, the procedure goes back to step S31, and the next charge waveform is extracted and the operation of counting the number of specific peak occurrences is continued.

If the counting for N revolutions of the tire is completed, a histogram representing a frequency distribution of the numbers of specific peak occurrences is constructed (step S35) and then the histogram is approximated by a Weibull distribution to calculate the scale parameter η and the shape parameter m of the probability density function of the Weibull distribution (step S36).

Finally, the internal pressure of the tire of the running vehicle is detected by comparing the calculated scale parameter η and shape parameter m with the P-W map 18M (step S37).

As described above, in the third embodiment, the amplitude of the charge potential distributed over a vehicle body resulting from the contact, separation, and friction between the tire and the road surface is monitored, and the internal pressure of the tire is detected from the time-varying waveform changing with the changes in the internal pressure of the tire. Therefore, the internal pressure of the tire can be detected with accuracy without installing a sensor on the tire.

In doing so, a histogram representing a frequency distribution of the numbers of specific peak occurrences is constructed from the time-varying waveform of the charged voltage; the scale parameter η and the shape parameter m of the probability density function of a Welbull distribution are obtained; and the internal pressure of the tire is detected using these scale parameter η and shape parameter m. As a result, the internal pressure of the tire can be detected with further improved accuracy by eliminating the influence of the unevenness of the road surface or the speed of the vehicle.

In the foregoing third embodiment, the internal pressure of the tire is detected by comparing the scale parameter η and shape parameter m calculated by the use of the time-varying waveform of charged voltage with the P-W map 68M. However, the arrangement may be such that the threshold $K_{p1}$ and the threshold $K_{p2}$ are set for the scale parameter η and the shape parameter m, respectively, and the internal pressure of the tire is detected as being high when $\eta \geq K_{p1}$ and $m \geq K_{p2}$ or as being low when $\eta < K_{p1}$ and $m < K_{p2}$.

Fourth Embodiment

Figure 20:
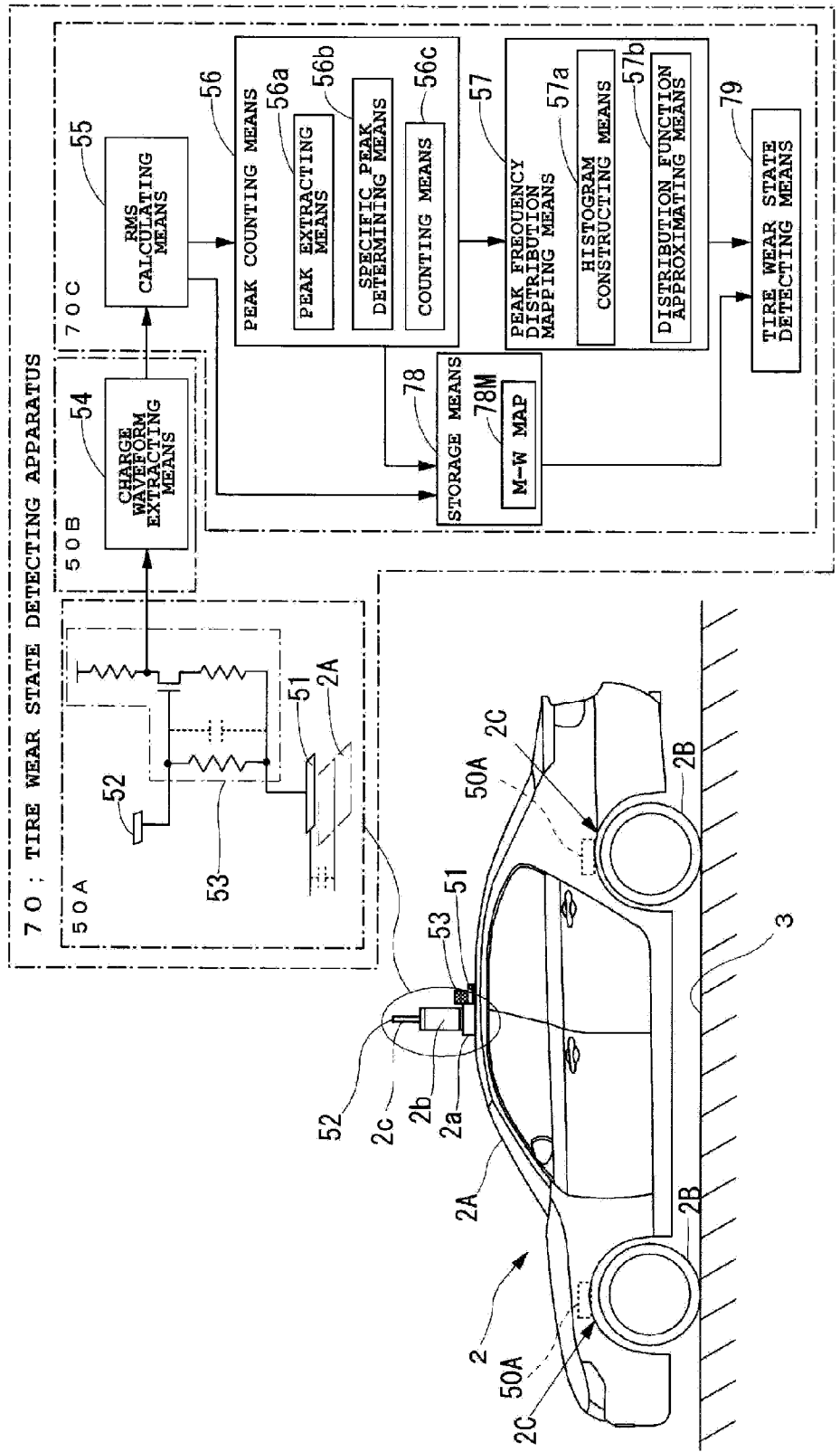
FIG. 20 is a schematic diagram showing a constitution of a tire wear state detecting apparatus in accordance with the fourth embodiment of the present invention.

FIG. 20 is a diagram showing a structure of a tire wear detecting apparatus 70 according to a fourth embodiment of the present invention.

The tire wear detecting apparatus 70 includes a sensing electrode 51, a reference electrode 52, a sensor amplifier 53, a charge waveform extracting means 54, an RMS (Root Mean Square) calculating means 55, a peak counting means 56, a peak frequency distribution mapping means 57, a storage means 78, and a tire wear detecting means 79.

The sensing electrode 51 and the respective means from the reference electrode 52 through the peak frequency distribution mapping means 57 are of the same structure as those of the second and third embodiments, and so the description thereof will be omitted.

The charge potential over the vehicle body 2A changes with the changes in the capacitance between the tire 2B and the road surface 3. And the capacitance between the tire 2B and the road surface 3 also changes with the state of contact and the strength of friction between the tire and the road surface. As tire wear progresses, the groove depth will become shallower and the block stiffness may undergo changes. With the changes in the surface condition of the tread, the state of contact and the strength of friction between the tire and the road surface may also undergo changes. Hence, the wear state of the tire can be detected by detecting the changes in the charge potential.

In the present embodiment, the storage means 78 stores not only the RMS value of the charge waveform for each revolution of the tire extracted by the RMS calculating means 55 and the number of specific peak occurrences for each revolution of the tire counted by the counting means 56c, but also an M-W map 78M representing a relationship between the wear state of the tire and the scale parameter η and the shape parameter m.

The M-W map 78M can be prepared by first constructing histograms representing the frequency distributions of numbers of specific peak occurrences which have been obtained by operating a test vehicle fitted with tires having different groove depths H and then obtaining the scale parameter η and the shape parameter m by approximating each of the histograms constructed for the different groove depths H by the probability density function of a Weibull distribution.

As the M-W map 78M, for example, a curved surface H (η, m) whose x-axis is the scale parameter η, y-axis the shape parameter m, and z-axis the groove depth of the tire or a table listing data on the groove depth H in each of the domains of the scale parameter η [η−Δη/2, η+Δη/2] and the shape parameter m [m−Δm/2, m+Δm/2] can be used.

The tire wear detecting means 79 detects the groove depth H, which is an indicator of the wear state of the tire, by comparing the scale parameter η and the shape parameter m of the probability density function of a Weibull distribution obtained by the peak frequency distribution mapping means 57 with the M-W map 78M stored in the storage means 78.

Figure 21A:
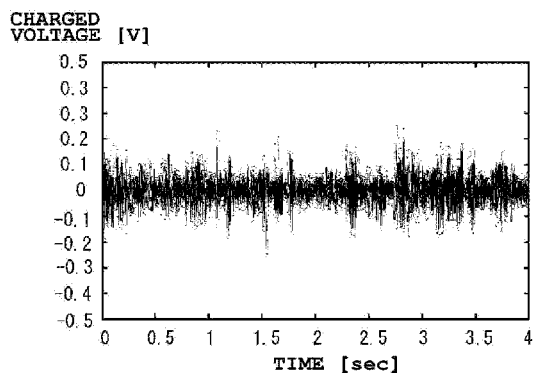
FIGS. 21(A) and 21(B) are a time-varying waveform of charged voltage and a histogram showing a frequency distribution of the numbers of specific peak occurrences of a new tire.
Figure 21B:
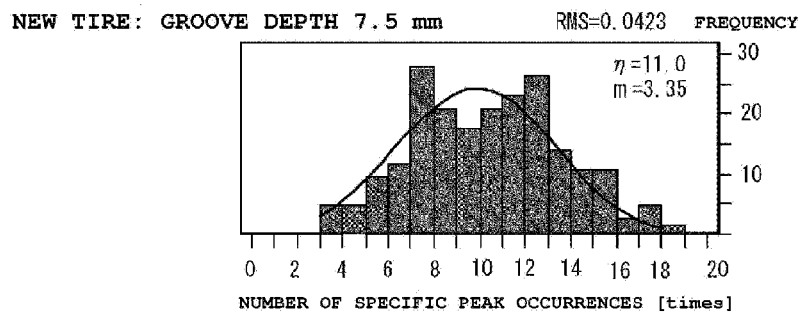
Figure 22A:
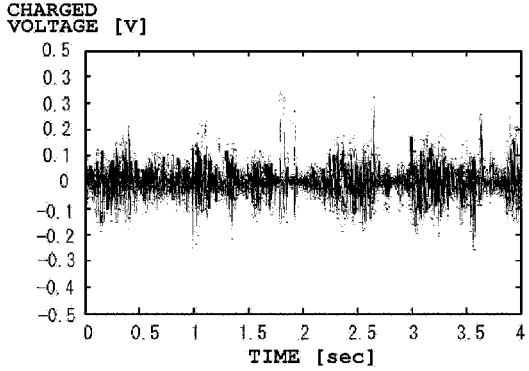
FIGS. 22(A) and 22(B) are a time-varying waveform of charged voltage and a histogram showing a frequency distribution of the numbers of specific peak occurrences of a worn tire.
Figure 22B:
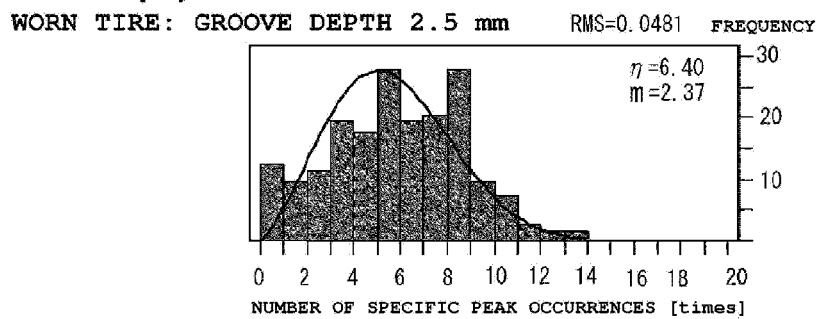

FIGS. 21A and 21B are a time-varying waveform of charged voltage and a histogram showing a frequency distribution of the numbers of specific peak occurrences, respectively, when the tire is not worn (hereinafter referred to as "new tire"). FIGS. 22A and 22B are a time-varying waveform of charged voltage and a histogram showing a frequency distribution of the numbers of specific peak occurrences, respectively, when the tire is worn (hereinafter referred to as "worn tire"). Note that the groove depth of the new tire employed is $H_0=7.5$ mm and the groove depth of the worn tire employed is H=2.5 mm.

On comparison of the scale parameters η and the shape parameters m of the probability density function by approximating the histogram for the new tire and the histogram for the worn tire by Weibull distributions shown by thick curves in their respective figures, it is found that both the scale parameter η and the shape parameter m of the probability density function are larger for the new tire (η=11.0, m=3.35) and both the scale parameter η and the shape parameter m are smaller for the worn tire (η=6.40, m=2.37).

Therefore, the groove depth, which is an indicator of the wear state of the tire, can be detected with accuracy by comparing the scale parameter η and the shape parameter m with the M-W map 78M stored in the storage means 78.

That is, if the scale parameter and the shape parameter of the probability density function of a Weibull distribution obtained by the peak frequency distribution mapping means 17 are denoted by $\eta_k$ and $m_k$, respectively, the groove depth is detected as $H_k$ when $\eta_k+\Delta\eta/2 \geq \eta \geq \eta_k+\Delta\eta/2$ and also $m_k+\Delta m/2 \geq m \geq m_k+\Delta m/2$. Here, $H_k$ is the groove depth when the scale parameter as listed in the M-W map 78M is $\eta_k$ and the shape parameter $m_k$.

Figure 23:
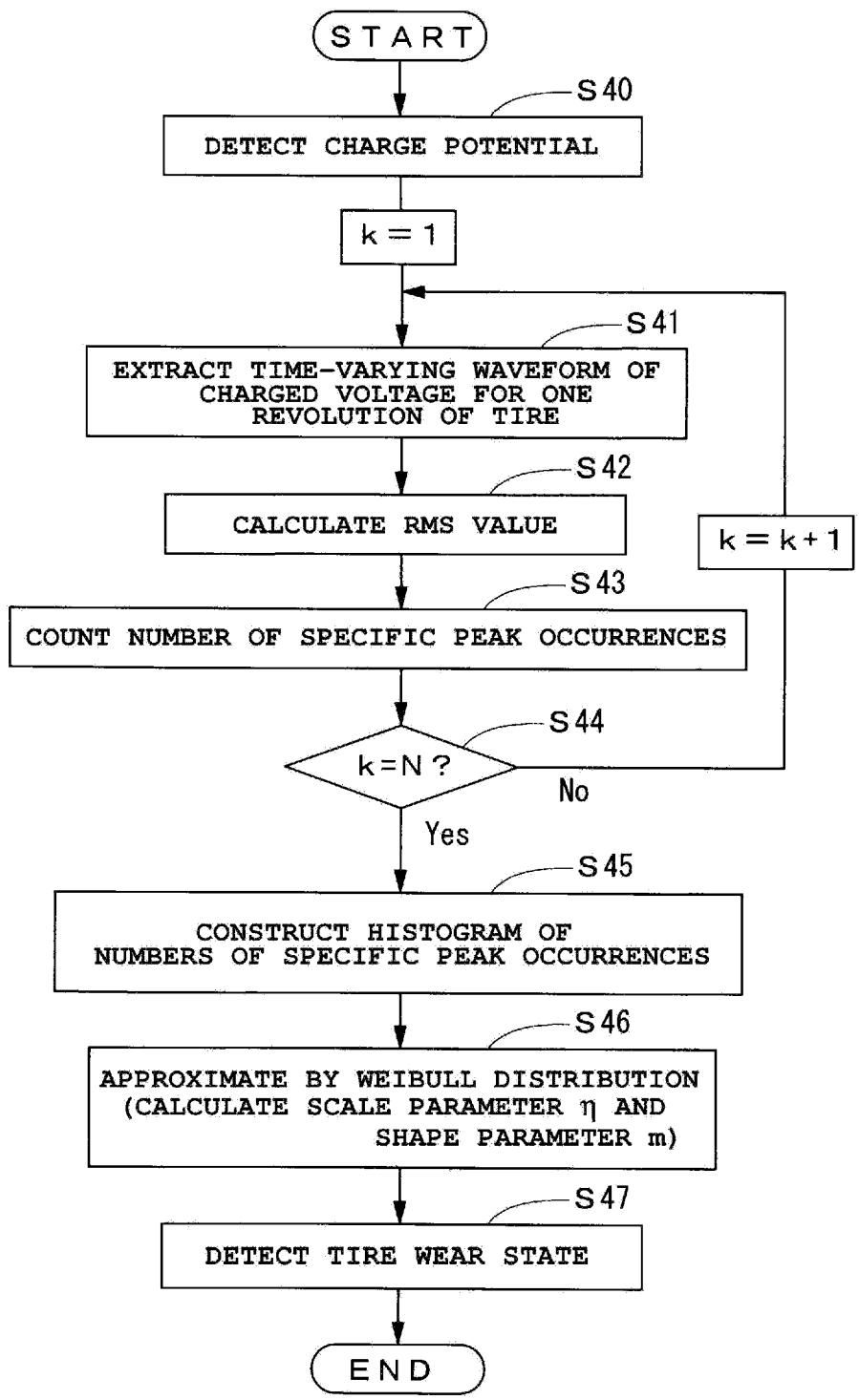
FIG. 23 is a flowchart showing a method for detecting the wear state of the tire.

Next, a description is given of a method for detecting the wear state of the tire using the tire wear detecting apparatus 70, with reference to the flowchart of FIG. 23.

First the changes in the charge potential over the vehicle body 2A changing with the changes in the capacitance between the tire 2B of a running vehicle 2 and the road surface 3 are detected as a time-varying waveform of charged voltage by the sensing electrode 51 capacitively coupled to the vehicle body 2A (step S40). Then a charge waveform, which is a time-varying waveform of charged voltage for each revolution of the tire, is sequentially extracted from the time-varying waveform of charged voltage (step S41).

Next, the RMS value of the extracted charge waveform for one revolution of the tire is calculated (step S42), and at the same time the number of specific peak occurrences, which is the number of specific peaks in the charge waveform for the one revolution of the tire, is counted (step S43).

Then it is determined whether the counting of specific peak occurrences for N revolutions of the tire has been completed or not (step S44)

If the counting for N revolutions of the tire is not completed, the procedure goes back to step S41, and the next charge waveform is extracted and the operation of counting the number of specific peak occurrences is continued.

If the counting for N revolutions of the tire is completed, a histogram representing a frequency distribution of the numbers of specific peak occurrences is constructed (step S45) and then the histogram is approximated by a Weibull distribution to calculate the scale parameter η and the shape parameter m of the probability density function of the Weibull distribution (step S46).

Finally, the groove depth of the tire of the running vehicle is detected by comparing the calculated scale parameter η and shape parameter m with the M-W map 78M (step S47).

As described above, in the fourth embodiment, the amplitude of the charge potential distributed over a vehicle body resulting from the contact, separation, and friction between the tire and the road surface is monitored, and the wear state of the tire is detected from the time-varying waveform changing with the changes in the state of tire wear. Therefore, the wear characteristics of the tire can be detected with accuracy without installing a sensor on the tire.

In doing so, a histogram representing a frequency distribution of the numbers of specific peak occurrences is constructed from the time-varying waveform of the charged voltage; the scale parameter η and the shape parameter m of the probability density function of a Welbull distribution are obtained; and the groove depth, which is an indicator of the wear state of the tire, is detected using these scale parameter η and shape parameter m. As a result, the accuracy of detection of the wear state of the tire can be further improved by eliminating the influence of the unevenness of the road surface or the speed of the vehicle.

In the foregoing fourth embodiment, the wear state of the tire is detected by comparing the scale parameter η and shape parameter m calculated by the use of the time-varying waveform of charged voltage with the M-W map 78M. However, the arrangement may be such that the threshold $K_{m1}$ and the threshold $K_{m2}$ are set for the scale parameter η and the shape parameter m, respectively, and the tire wear is determined as being not advanced when $\eta \geq K_{m1}$ and $m \geq K_{m2}$ or as being advanced when $\eta < K_{m1}$ and $m < K_{m2}$.

Fifth Embodiment

Figure 24:
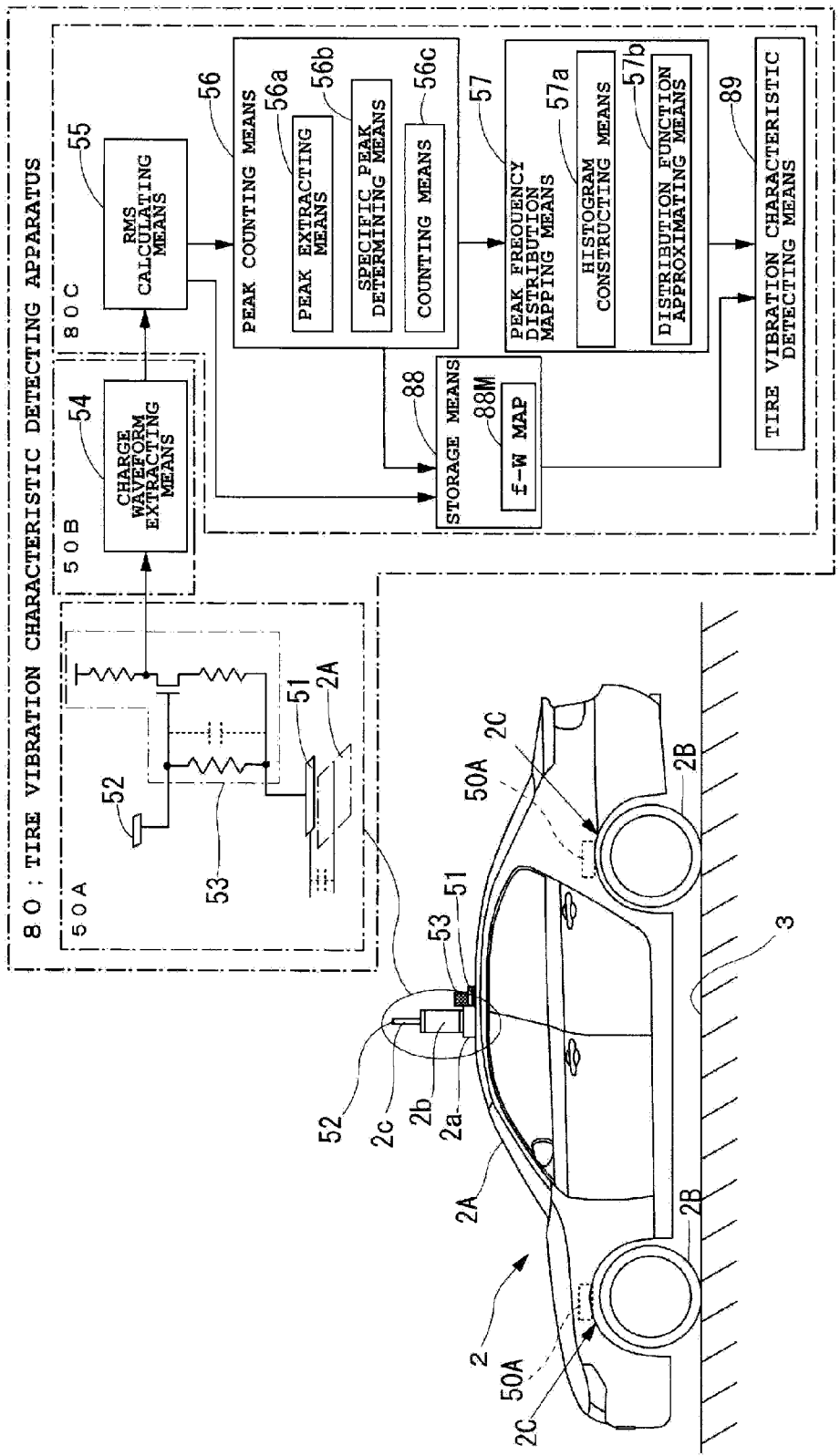
FIG. 24 is a schematic diagram showing a constitution of a tire vibration characteristic detecting apparatus in accordance with the fifth embodiment of the present invention.

FIG. 24 is a diagram showing a structure of a tire vibration characteristic detecting apparatus 80 according to a fifth embodiment.

The tire vibration characteristic detecting apparatus 80 includes a sensing electrode 51, a reference electrode 52, a sensor amplifier 53, a charge waveform extracting means 54, an RMS (Root Mean Square) calculating means 55, a peak counting means 56, a peak frequency distribution mapping means 57, a storage means 88, and a tire vibration characteristic detecting means 89.

The sensing electrode 51 and the respective means from the reference electrode 52 through the peak frequency distribution mapping means 57 are of the same structure as those of the second to fourth embodiments, and so the description thereof will be omitted.

The charge potential over the vehicle body 2A changes with the changes in the capacitance between the tire 2B and the road surface 3. And the capacitance between the tire 2B and the road surface 3 also changes with the state of contact and the strength of friction between the tire and the road surface. When the tread rubber deforms cyclically due to the wet skid resistance or the rolling resistance, the state of contact and the strength of friction between the tire and the road surface may also undergo changes. Hence, the vibration characteristics of the tire can be detected by detecting the changes in the charge potential.

In the present embodiment, the storage means 88 stores not only the RMS value of the charge waveform for each revolution of the tire extracted by the RMS calculating means 55 and the number of specific peak occurrences for each revolution of the tire counted by the counting means 56c, but also an f-W map 88M representing a relationship between the vibration characteristics of the tire and the scale parameter $\eta$ and the shape parameter m. In the present embodiment, the indicator of the vibration characteristics of the tire employed is the frequency of rubber deformation (hereinafter referred to as "deformation frequency") f caused by the wet skid resistance or the rolling resistance.

The f-W map 88M can be prepared by first constructing histograms representing the frequency distributions of numbers of specific peak occurrences which have been obtained by operating a test vehicle fitted with tires having different vibration characteristics, or deformation frequencies, and then obtaining the scale parameter $\eta$ and the shape parameter m by approximating each of the histograms constructed for the different deformation frequencies by the probability density function of a Weibull distribution.

As the f-W map 88M, for example, a curved surface $f(\eta, m)$ whose x-axis is the scale parameter $\eta$, y-axis the shape parameter m, and z-axis the deformation frequency or a table listing data on the deformation frequency f in each of the domains of the scale parameter $\eta$ $[\eta-\Delta\eta/2, \eta+\Delta\eta/2]$ and the shape parameter m $[m-\Delta m/2, m+\Delta m/2]$ can be used.

The tire vibration characteristic detecting means 89 detects the deformation frequency, which is an indicator of the vibration characteristics of the tire, by comparing the scale parameter $\eta$ and the shape parameter m of the probability density function of a Weibull distribution obtained by the peak frequency distribution mapping means 57 with the f-W map 88M stored in the storage means 88.

Figure 25A:
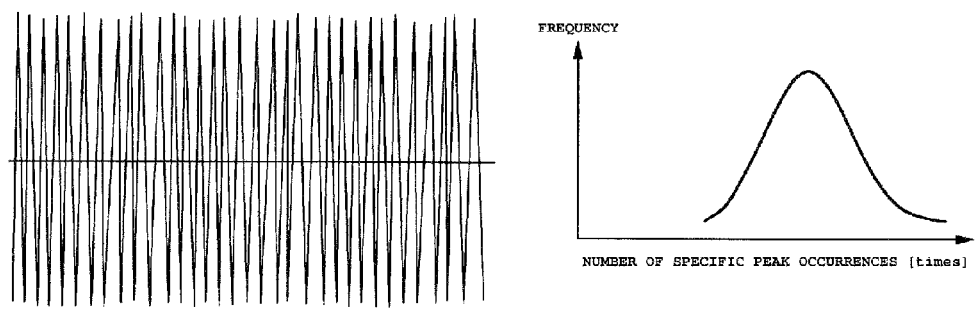
FIGS. 25(A) and 25(B) are diagrams showing time-varying waveforms of charged voltage and their Weibull distributions.
Figure 25B:
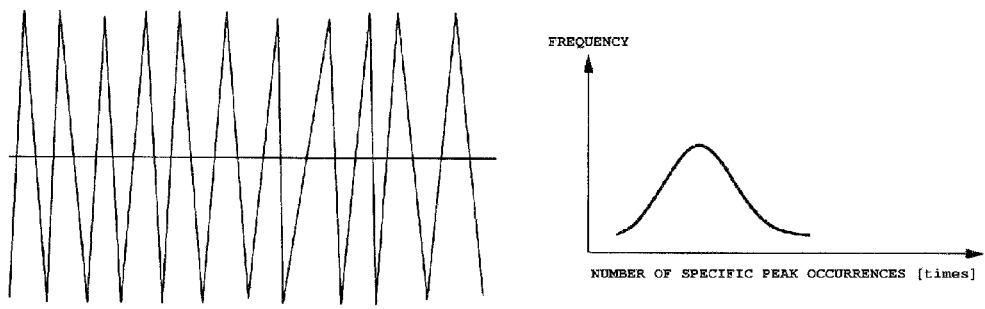

FIG. 25A is diagrams of approximation by the probability density function of a Weibull distribution of the histogram showing a frequency distribution of the numbers of specific peak occurrences when the deformation due to the wet skid resistance has occurred. FIG. 25B is diagrams of approximation by the probability density function of a Weibull distribution of the histogram showing a frequency distribution of the numbers of specific peak occurrences when the deformation due to the rolling resistance has occurred.

The deformation frequency of deformation due to the rolling resistance is within the range of 10 Hz to 100 Hz, whereas the deformation frequency of deformation due to the wet skid resistance is within the range of 10000 Hz to 100000 Hz.

The scale parameter $\eta$ changes with the number of peaks, whereas the shape parameter m changes with the variation in the number of peaks. The deformation frequency of deformation due to the wet skid resistance is higher than the deformation frequency of deformation due to the rolling resistance. Thus, the scale parameter $\eta$ of the vibration characteristics of deformation due to the wet skid resistance is greater than the scale parameter $\eta$ of the vibration characteristics of deformation due to the rolling resistance. It is to be noted that the smaller the variation, the larger the shape parameter m will be, and therefore the vibration characteristics of deformation due to the wet skid resistance whose deformation frequency is higher and frequency of specific peak occurrences is also higher have greater shape parameters m.

Therefore, the deformation frequency, which is an indicator of the vibration characteristics of the tire, can be detected with accuracy by comparing the scale parameter $\eta$ and the shape parameter m with the f-W map 88M stored in the storage means 88.

Figure 26:
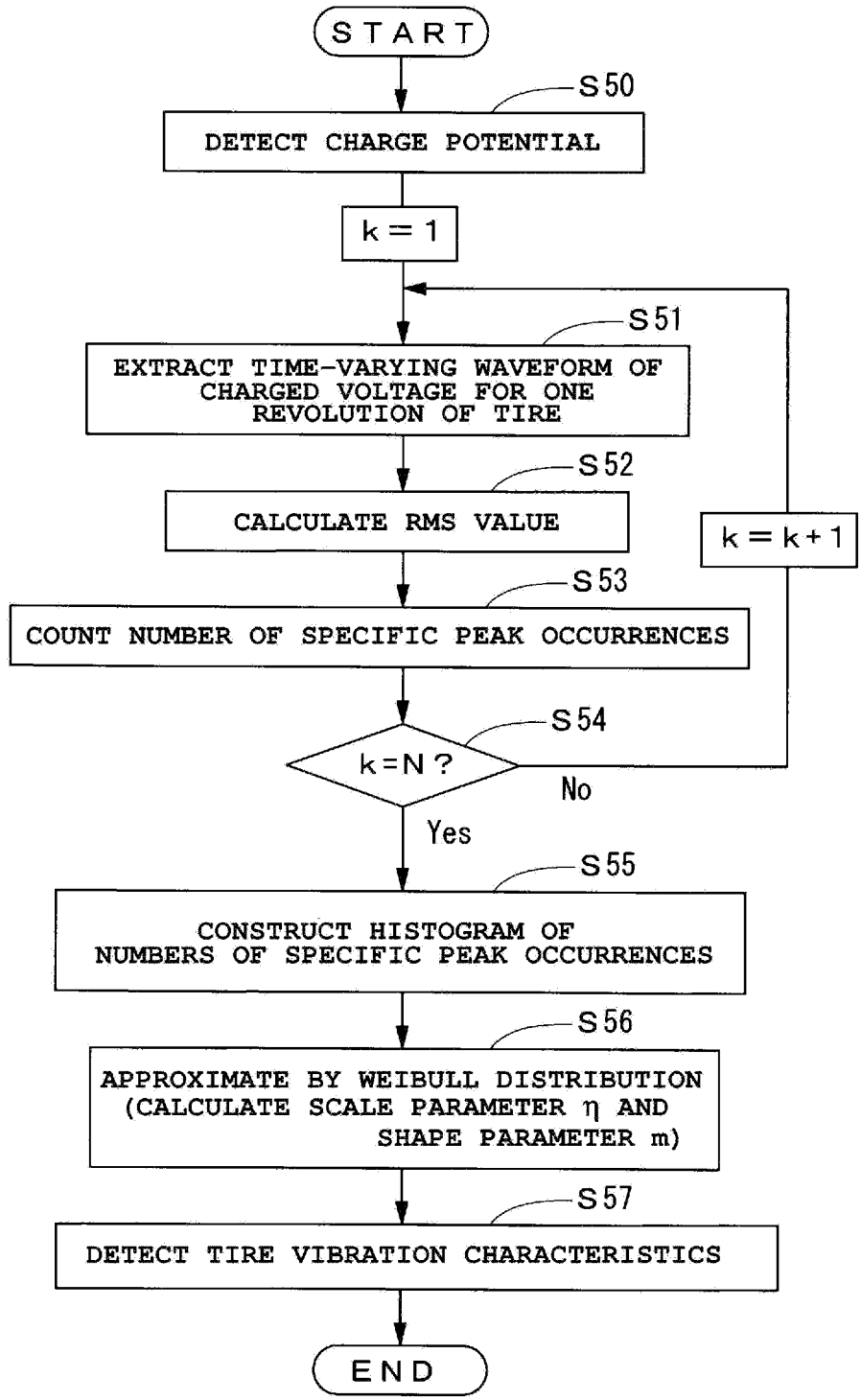
FIG. 26 is a flowchart showing a method for detecting vibration characteristics of the tire.

Next, a description is given of a method for detecting the vibration characteristics of the tire, with reference to the flowchart of FIG. 26.

First the changes in the charge potential over the vehicle body 2A changing with the changes in the capacitance between the tire 2B of a running vehicle 2 and the road surface 3 are detected as a time-varying waveform of charged voltage by the sensing electrode 51 capacitively coupled to the vehicle body 2A (step S50). Then a charge waveform, which is a time-varying waveform of charged voltage for each revolution of the tire, is sequentially extracted from the time-varying waveform of charged voltage (step S51).

Next, the RMS value of the extracted charge waveform for one revolution of the tire is calculated (step S52), and at the same time the number of specific peak occurrences, which is the number of specific peaks in the charge waveform for the one revolution of the tire, is counted (step S53).

Then it is determined whether the counting of specific peak occurrences for N revolutions of the tire has been completed or not (step S54)

If the counting for N revolutions of the tire is not completed, the procedure goes back to step S51, and the next charge waveform is extracted and the operation of counting the number of specific peak occurrences is continued.

If the counting for N revolutions of the tire is completed, a histogram representing a frequency distribution of the numbers of specific peak occurrences is constructed (step S55) and then the histogram is approximated by a Weibull distribution to calculate the scale parameter $\eta$ and the shape parameter m of the probability density function of the Weibull distribution (step S56).

Finally, the deformation frequency of the tire of the running vehicle is detected by comparing the calculated scale parameter $\eta$ and shape parameter m with the f-W map 88M (step S57).

As described above, in the fifth embodiment, the amplitude of the charge potential distributed over a vehicle body resulting from the contact, separation, and friction between the tire and the road surface is monitored, and the vibration state of the tire is detected from the time-varying waveform changing with the changes in the internal pressure of the tire. Therefore, the vibration characteristics of the tire can be detected with accuracy without installing a sensor on the tire.

In doing so, a histogram representing a frequency distribution of the numbers of specific peak occurrences is constructed from the time-varying waveform of the charged voltage; the scale parameter $\eta$ and the shape parameter m of the probability density function of a Welbull distribution are obtained; and the deformation frequency, which is an indicator of the vibration characteristics of the tire, is detected using these scale parameter $\eta$ and shape parameter m. As a result, the accuracy of detection of the vibration characteristics of the tire can be further improved by eliminating the influence of the unevenness of the road surface or the speed of the vehicle.

It should be noted that the vibration characteristics of the tire in relation to the deformation of tread rubber have conventionally been obtained indirectly by measuring the temperature dependence of tan δ and doing a temperature-vibration conversion as shown in FIG. 27. However, as described in this embodiment, it is now possible to detect the vibration characteristics of the tire directly by monitoring the amplitude of the charge potential distributed over the vehicle body.

In the foregoing fifth embodiment, the time-varying waveform of charged voltage is directly used in determining the specific peaks. However, the specific peaks due to the wet skid resistance may be determined, for instance, using the time-varying waveform of charged voltage which has been passed through a bandpass filter of 5000 Hz to 20000 Hz. Note that in determining specific peaks attributable to the rolling resistance, a bandpass filter of 5 Hz to 200 Hz may be used.

In the foregoing specification, the invention has been described with reference to specific embodiments thereof. However, the technical scope of this invention is not to be considered as limited to those embodiments. It will be evident to those skilled in the art that various modifications and changes may be made thereto without departing from the broader spirit and scope of the invention. It will also be evident from the scope of the appended claims that all such modifications are intended to be included within the technical scope of this invention.

INDUSTRIAL APPLICABILITY

The present invention provides its applicability in such industrial fields as transportation, agriculture, mining, forestry, fishery, construction, manufacturing, electricity and information and communication. It goes without saying that the invention is also widely applicable in many other industrial fields.

DESCRIPTION OF REFERENCE NUMERALS 1 measuring apparatus
10 detecting unit
11 sensing electrode
12 reference electrode
13 sensor amplifier
14 support member
15 vibration-absorbing member
20 data processing unit
21 CPU
22 ROM
23 RAM
24 storage unit
31 A/D conversion unit
32 filter unit
33 measuring unit
34 monitoring unit
41-44 electrode

The invention claimed is:

1. A measuring method, comprising:
disposing a first electrode on a vehicle body and a second electrode spaced apart from the first electrode;
detecting a charge potential between the first electrode and the second electrode, the charge potential distributed over the vehicle body or a tire resulting from contact, separation, and friction between a tire and a road surface;
monitoring an amplitude of the charge potential detected in the detecting;
counting plural times a number of specific peaks in each unit period, which is a number of peaks of variation in charge potential occurring in a time-varying waveform of the amplitude larger than a mean of the amplitude in each unit period; and
determining a state of the road surface under the tire or detecting at least one condition of the tire including an internal pressure state, a wear state, or vibration characteristics of the tire from a frequency of occurrences of the specific peaks.

2. The measuring method according to claim 1, further comprising extracting a time-varying waveform of the amplitude and estimating a state of road surface under the tire from a change in the time-varying waveform of the amplitude changing with changes in the state of the road surface.

3. The measuring method according to claim 1, further comprising extracting a time-varying waveform of the amplitude and detecting an internal pressure state of the tire from a change in the time-varying waveform of the amplitude changing with changes in the internal pressure of the tire.

4. The measuring method according to claim 1, further comprising extracting a time-varying waveform of the amplitude and detecting a wear state of the tire from a change in the time-varying waveform of the amplitude changing with changes in the wear state of the tire.

5. The measuring method according to claim 1, further comprising extracting a time-varying waveform of the amplitude and detecting vibration characteristics of the tire from a change in the time-varying waveform of the amplitude changing with changes in the vibration characteristics of the tire.

6. The measuring method according to claim 1, wherein the counting comprises obtaining an RMS value in a unit period from the time-varying waveform of the amplitude as a mean of the amplitude in the unit period.

7. The measuring method according to claim 6, wherein the counting comprises extracting a positive-side peak and a negative-side peak from the time-varying waveform of the amplitude, calculating a peak value difference, which is the difference between the amplitude value of the positive-side peak and the amplitude value of the negative-side peak, determining the positive-side peak or the negative-side peak as a specific peak when the peak value difference exceeds the RMS value, and counting the number of specific peaks thus determined, and wherein the estimating or detecting comprises finding a frequency distribution of the numbers of specific peaks in a unit period and estimating a state of road surface under the tire or detecting an internal pressure state, a wear state, or vibration characteristics of the tire from the frequency of specific peak occurrences.

8. The measuring method according to claim 7, wherein the estimating or detecting comprises calculating a scale parameter and a shape parameter of probability density function of a Weibull distribution by approximating the frequency distribution by the Weibull distribution and estimating a state of road surface under the tire or detecting an internal pressure state, a wear state, or vibration characteristics of the tire from the calculated scale parameter and shape parameter or from the calculated shape parameter.

9. The measuring method according to claim 1, wherein the first electrode includes a sensing electrode and the second electrode includes a reference electrode.

10. The measuring method according to claim 1 further comprising providing a sensor amplifier to detect the charge potential and to amplify a signal of the charge potential.

11. A measuring apparatus comprising:
a first electrode disposed on a vehicle body;
a second electrode spaced apart from the first electrode;
a detecting unit configured to detect charge potential between the first electrode and the second electrode, the charge potential distributed over the vehicle body or a tire resulting from contact, separation, and friction between a tire and a road surface; and
a monitoring unit configured to monitor an amplitude of the charge potential detected by the detecting unit and to count plural times a number of specific peaks in each unit period, which is a number of peaks of variation in charge potential occurring in a time-varying waveform of amplitude larger than a mean of amplitude in each unit period, thereby the monitoring unit determining a state of the road surface under the tire or detecting an internal pressure state, a wear state, or vibration characteristics of the tire from a frequency of specific peak occurrences.

12. The measuring apparatus according to claim 11, wherein the first electrode includes a sensing electrode and the second electrode includes a reference electrode.

13. The measuring apparatus according to claim 11 further comprising a sensor amplifier configured to detect the charge potential and to amplify a signal of the charge potential.

* * * * *